US011268892B2

(12) United States Patent
Sulchek et al.

(10) Patent No.: US 11,268,892 B2
(45) Date of Patent: *Mar. 8, 2022

(54) METHODS FOR CONTINUOUS SORTING OF CELLS BASED ON MOLECULAR ADHESION

(71) Applicant: Georgia Tech Research Corporation, Atlanta, GA (US)

(72) Inventors: Todd Sulchek, Atlanta, GA (US); Alexander Alexeev, Atlanta, GA (US); Bushra Tasadduq, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 245 days.

This patent is subject to a terminal disclaimer.

(21) Appl. No.: 16/348,520

(22) PCT Filed: Nov. 8, 2017

(86) PCT No.: PCT/US2017/060662
§ 371 (c)(1),
(2) Date: May 9, 2019

(87) PCT Pub. No.: WO2018/089512
PCT Pub. Date: May 17, 2018

(65) Prior Publication Data
US 2019/0360909 A1 Nov. 28, 2019

Related U.S. Application Data

(60) Provisional application No. 62/419,534, filed on Nov. 9, 2016.

(51) Int. Cl.
*B01L 3/00* (2006.01)
*G01N 15/10* (2006.01)
(Continued)

(52) U.S. Cl.
CPC .... *G01N 15/1056* (2013.01); *B01L 3/502761* (2013.01); *B01L 3/502776* (2013.01);
(Continued)

(58) Field of Classification Search
None
See application file for complete search history.

(56) References Cited

U.S. PATENT DOCUMENTS

2007/0026418 A1 2/2007 Fuchs et al.
2007/0072290 A1 3/2007 Hvichia
(Continued)

FOREIGN PATENT DOCUMENTS

CN 102083997 6/2011

OTHER PUBLICATIONS

International Search Report and Written Opinion from application No. PCT/US2017/060662 dated Jan. 9, 2018 (16 pages).
(Continued)

*Primary Examiner* — Rebecca M Giere
(74) *Attorney, Agent, or Firm* — Troutman Pepper Hamilton Sanders LLP; Ryan A. Schneider

(57) ABSTRACT

Embodiments of the present disclosure can include a method comprising: providing a plurality of cells to a microchannel, the microchannel coated in at least one cell adhesion entity and comprising a compressive surface and a first outlet, the compressive surface defining a compression gap, flowing the plurality of cells through the microchannel, wherein the flowing comprises: compressing the plurality of cells underneath the compressive surface; and exposing the plurality of cells to the at least one cell adhesion entity, wherein the exposing causes a first portion of the cells having a first adhesion property to temporarily bind to the cell adhesion entity; and collecting the first portion of cells at the first outlet; wherein the compression gap has a height of from 75% to 95% an average diameter of the plurality of cells.

20 Claims, 11 Drawing Sheets

(51) Int. Cl.
*G01N 1/34* (2006.01)
*G01N 33/50* (2006.01)

(52) U.S. Cl.
CPC ........... *G01N 1/34* (2013.01); *G01N 33/5005* (2013.01); *B01L 2200/0652* (2013.01); *B01L 2200/0668* (2013.01); *B01L 2300/0877* (2013.01); *B01L 2300/16* (2013.01); *B01L 2400/086* (2013.01); *G01N 2015/1006* (2013.01); *G01N 2015/1081* (2013.01)

(56) References Cited

U.S. PATENT DOCUMENTS

| | | |
|---|---|---|
| 2014/0227777 A1 | 8/2014 | Choi et al. |
| 2016/0139012 A1 | 5/2016 | D'Silva et al. |

OTHER PUBLICATIONS

Wang, et al., "Stiffness Dependent Separation of Cells in a Microfluidic Device," Public Library of Science One, vol. 8, Iss. 10, Oct. 15, 2013, pp. 1-10.

Wang, et al., "Microflulidic Cellular Enrichment and Separation Through Differences in Viscoelastic Deformation," Lab on a chip, vol. 15 (2015) pp. 532-540.

Search Report from European application No. 17869012.9 dated Apr. 15, 2020 (8 pages).

METHODS FOR CONTINUOUS SORTING OF CELLS BASED ON MOLECULAR ADHESION

CROSS-REFERENCE TO RELATED APPLICATIONS

This application, filed Nov. 8, 2017, claims the benefit of U.S. Provisional Patent Application No. 62/419,534, filed Nov. 9, 2016, titled "Microfluidic Device For Adhesion Sorting of Cells with Ridged Microchannels," the entire contents and substance of which are hereby incorporated by reference as if fully set forth below.

STATEMENT OF FEDERALLY SPONSORED RESEARCH

This invention was made with Government support under Grant Number CBET-0932510 awarded by the National Science Foundation and Grant Number 1R1EB020977-01 awarded by the NIH. The Government has certain rights in the invention.

BACKGROUND

Cell molecular interactions can regulate physiological processes, such as cell homing, immune modulation, and cancer metastasis. Identifying and isolating cells that express desired molecular surface markers can be helpful to a variety of applications in the biological sciences, cell therapy, and medical diagnostics.

BRIEF SUMMARY

Embodiments of the present disclosure can include a method comprising: providing a plurality of cells to a microchannel, the microchannel coated in at least one cell adhesion entity and comprising a compressive surface and a first outlet, the compressive surface defining a compression gap; flowing the plurality of cells through the microchannel, wherein the flowing comprises: compressing the plurality of cells underneath the compressive surface; and exposing the plurality of cells to the at least one cell adhesion entity, wherein the exposing causes a first portion of the cells having a first adhesion property to temporarily bind to the cell adhesion entity; and collecting the first portion of cells at the first outlet; wherein the compression gap has a height of from 75% to 95% an average diameter of the plurality of cells.

Embodiments of the present disclosure can include a method comprising: flowing a cell medium through a microchannel containing at least one adhesion molecule, the cell medium comprising a first cell having a first adhesion property and a second cell having a second adhesion property; compressing the first and second cells as they flow through the microchannel, wherein the compressing causes at least one of the first and second cells to temporarily bind to the adhesion molecule; and collecting one or both of the first and second cells at a first outlet of the microchannel and collecting one or both of the first and second cells at a second outlet of the microchannel.

Embodiments of the present disclosure can include a method comprising: providing a cell medium to a microchannel, the cell medium comprising a first cell having a first adhesion property and a second cell having a second adhesion property, wherein the cell medium is provided to the microchannel at a flow velocity of from 75 mm/s to 300 mm/s; flowing the cell medium within the microchannel, the microchannel defining a compression gap and coated in at least one adhesion molecule, wherein the flowing comprises: compressing the first cell and the second cell as they pass through the compression gap; exposing the first cell and the second cell to the adhesion molecule, wherein the exposing causes the first and second cells to temporarily bind to the adhesion molecule; and collecting one or both of the first and second cells at a first outlet of the microchannel and collecting one or both of the first and second cells at a second outlet of the microchannel.

Embodiments of the present disclosure can include a device comprising: an inlet for flowing a cell medium comprising a plurality of cells into the device at a flow velocity; a first planar wall and a second planar wall, the first planar wall having a compressive surface protruding normal to the first planar wall and defining a compression gap between the second planar wall and the compressive surface; a plurality of outlets for collecting sorted portions of the plurality of cells wherein the sorted portions share adhesion properties; and at least one cell adhesion entity disposed on one or both of the first planar wall and the second planar wall; wherein the compression gap has a height of from 75% to 95% an average diameter of the plurality of cells.

Embodiments of the present disclosure can include a system comprising a microchannel having a first planar wall and a second planar wall, the microchannel comprising a compressive surface protruding outwardly from the first planar wall and defining a compression gap between the second planar wall and the compressive surface, wherein the microchannel is coated with at least one adhesion molecule; an inlet for flowing a cell medium into the microchannel at a flow velocity, the cell medium comprising a first cell having a first adhesion property and a second cell having a second adhesion property; a first outlet for collecting one or both of the first and second cells and a second outlet for collecting one or both of the first and second cells; wherein the plurality of cells are compressed as they flow through the compression gap, such that they temporarily bind with the adhesion molecule; and wherein the compression gap has a height of about 80% to about 90% an average diameter of the plurality of cells.

In some embodiments, the microchannel of any of the above-described systems, methods, and devices can further comprise a first wall and a second wall, the first and second walls being substantially planar to each other and the compressive surface is disposed on the first and/or the second wall such that the compressive surface protrudes normal to the first and/or second wall and defines the compression gap between the compressive surface and a surface of the first and/or second wall. In some embodiments, the microchannel of any of the above-described systems, methods, and devices can further comprise at least one inlet. In some embodiments, the microchannel of any of the above-described systems, methods, and devices can further comprise at least two outlets.

In any of the above-described systems, methods, and devices, at least a portion of the plurality of cells can undergo a compression due to the compressive surface.

In any of the above-described systems, methods, and devices, the microchannel can comprise from 1 to 7 compressive surfaces. In some embodiments, the microchannel comprises seven compressive surfaces and at least a portion of the plurality of cells undergo seven compressions. In of the above-described systems, methods, and devices, wherein the microchannel comprises more than one compressive surface, the microchannel can further comprise a flow space disposed between respective compressive surfaces. In of the above-described systems, methods, and devices, the width of the flow space can be from 50 to 500 microns. In some embodiments, the width of the flow space can be from 100 to 300 microns. In some embodiments of any of the above-described systems, methods, and devices, the compressive surface can comprise a ridge.

In some embodiments of any of the above-described systems, methods, and devices, the compressive surface(s) can be oriented at an angle of from 25 degrees to 70 degrees measured with respect to the central axis of the microchannel. In other embodiments, the compressive surface(s) can be oriented at an angle of from 30 degrees to 60 degrees measured with respect to the central axis of the microchannel.

In some embodiments of any of the above-described systems, methods, and devices, the compression gap can have a height of from 80% to 90% the average cell diameter.

In some embodiments of any of the above-described systems, methods, and devices, the plurality of cells or cell medium can be provided to the microchannel at a flow velocity of from 10 mm/s to 750 mm/s. In other embodiments, the flow velocity can be about 75 mm/sec.

In some embodiments of any of the above-described systems, methods, and devices, a sheath flow can be provided to the plurality of cells and/or cell medium, to cause the cells and/or cell medium to flow through the microchannel.

In some embodiments of any of the above-described systems, methods, and devices, the above-mentioned cells can comprise a cell surface receptor and the cell adhesion entity temporarily binds to the cell surface receptor.

In some embodiments of any of the above-described systems, methods, and devices, one or more cells or portions of cells can have different adhesion properties. In some embodiments of any of the above-described systems and methods cells having different adhesion properties can follow different trajectories through the microchannel.

In some embodiments of any of the above-described systems, methods, and devices, from 40,000 to 100,000 cells can be sorted per minute based on one or more cell adhesion properties.

DETAILED DESCRIPTION

Figure 1A:
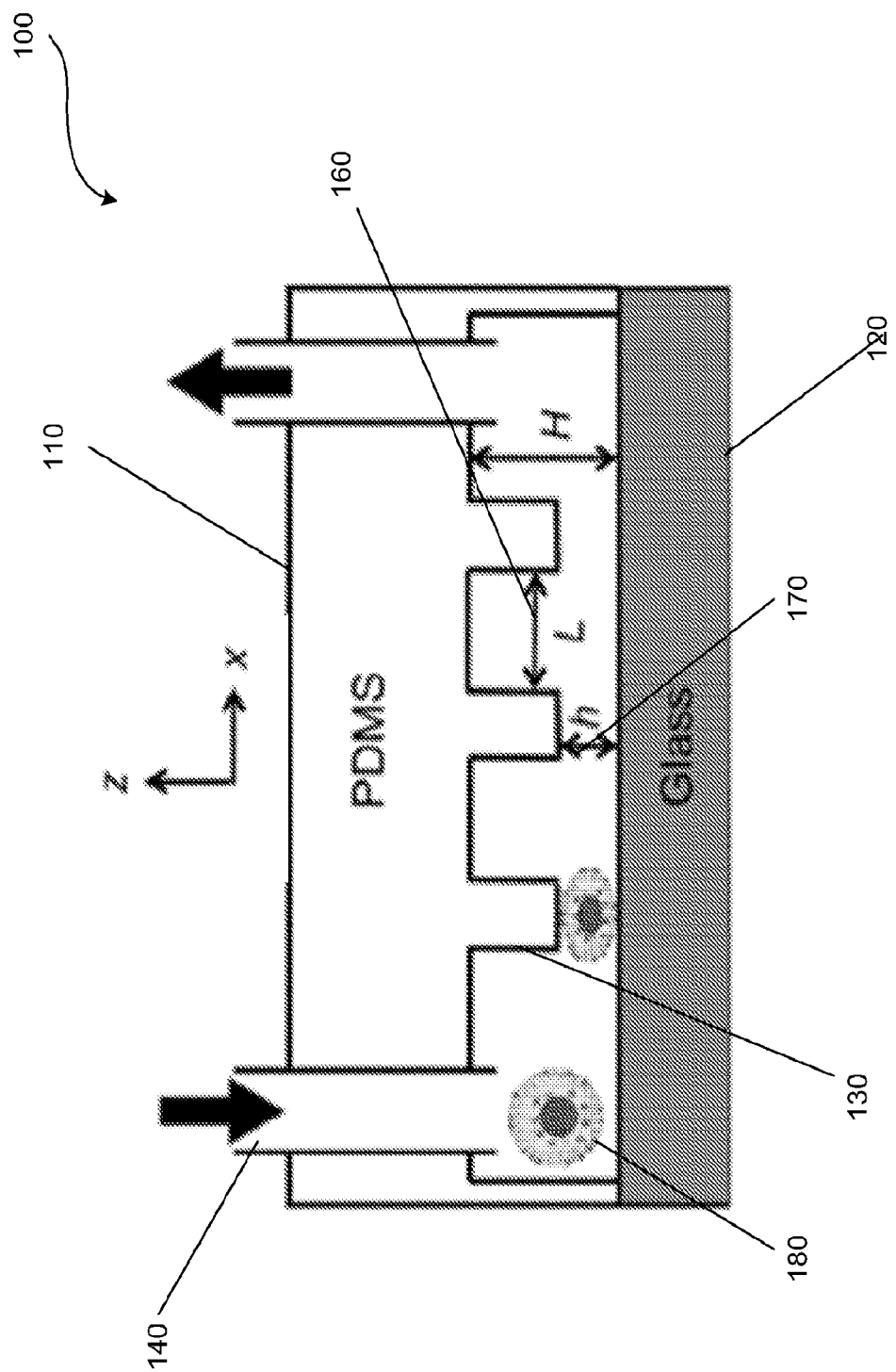
FIG. 1a is a cross-sectional diagram of a cell sorting device, in accordance with one or more embodiments of the present disclosure.

Although some embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. The disclosure is capable of other embodiments and of being practiced or carried out in various ways. Also, in describing the embodiments, specific terminology may be resorted to for the sake of clarity.

As used in the specification and the appended claims, the singular forms "a," "an" and "the" include plural referents unless the context clearly dictates otherwise.

Also, in describing the embodiments, terminology will be resorted to for the sake of clarity. It is intended that each term contemplates its broadest meaning as understood by those skilled in the art and includes all technical equivalents which operate in a similar manner to accomplish a similar purpose.

Ranges can be expressed herein as from "about" or "approximately" one particular value and/or to "about" or "approximately" another particular value. When such a range is expressed, another embodiment includes from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

Known methods for sorting cells based on adhesion, such as fluorescence activated cell sorting (FACS) or magnetic nanoparticle tagging for use in MACS, may not allow for fractionation into multiple outlets of finer sensitivity to a molecule of interest. Other methods for what might be considered continuous sorting based on adhesion are incapable of providing high-throughput application. Additionally, other microfluidic applications can rely on a process that results in cell capture instead of continuous sorting where cells having certain affinity for the adhesive molecule attach to the device and can only be released by shear forces that can damage cells. Embodiments of the presently disclosed systems and methods improve upon known devices in that they are capable of high-throughput separation of cells based on differences in molecular adhesion, allowing for fractionation of cells based on their tendency to attach to a surface, substrate, or another cell—a process mediated by interactions between cell adhesion entities (e.g., adhesion molecules) providing specificity to a cell surface receptor. The described embodiments can promote compression and relaxation of cells as cells move through a microchannel coupled with transient interaction between cells and cell adhesion entities within the microchannel. The compressions can constrict the one or more cells as the cells pass through the compressive space (e.g., a compression gap) during which the cells can transiently interact with the cell adhesion entity disposed upon the interfaces of the microchannel. As cells interact with the cell adhesion entity, net forces can be altered to redirect the flowing cells on a specific trajectory towards certain portions of the channel. For instance, cells with high expression of target molecule (influenced by the types of cell adhesion entity) can be concentrated toward one side of the microchannel for collection.

The compressive spaces (e.g., compression gaps) and relaxation spaces can be designed to promote an increase in surface area for transient or temporary interaction between the cell adhesion molecule and the cell surface—which can be substantially without the influence of biomechanical properties such as stiffness and viscoelasticity. Some embodiments of the pending disclosure can also feature the ability to obtain high throughput and high flow rate sorting of cells based on adhesion properties.

Embodiments of the present disclosure can comprise several systems and methods for sorting cells based on adhesion properties. An exemplary method of the present disclosure can include one or more of the following: (1) providing a plurality of cells to a microchannel, the microchannel coated in at least one adhesion molecule and comprising a compressive surface and a first outlet, the compressive surface defining a compression gap; (2) providing a cell medium to a microchannel, the cell medium comprising a first cell having a first adhesion property and a second cell having a second adhesion property, wherein the cell medium is provided to the microchannel at a flow velocity of from 10 mm/second to 100 mm/second; (3) flowing the plurality of cells through the microchannel; 4) flowing a cell medium through a microchannel containing at least one adhesion molecule, the cell medium comprising a first cell having a first adhesion property and a second cell having a second adhesion property; (5) compressing the plurality of cells underneath the compressive surface; (6) compressing the first and second cells as they flow through the microchannel, wherein the compressing causes at least one of the first and second cells to temporarily bind to the adhesion molecule; (7) exposing the plurality of cells to the at least one adhesion molecule, wherein the exposing causes a first portion of the cells having a first adhesion property to temporarily bind to the adhesion molecule; (8) collecting the first portion of cells at the first outlet; and (9) collecting one or both of the first and second cells at a first outlet of the microchannel and collecting one or both of the first and second cells at a second outlet of the microchannel.

In some embodiments, a method can comprise: providing a plurality of cells to a microchannel, the microchannel coated in at least one adhesion molecule and comprising a compressive surface and a first outlet, the compressive surface defining a compression gap; flowing the plurality of cells through the microchannel, wherein the flowing comprises compressing the plurality of cells underneath the compressive surface; and exposing the plurality of cells to the at least one adhesion molecule, wherein the exposing causes a first portion of the cells having a first adhesion property to temporarily bind to the adhesion molecule; and collecting the first portion of cells at the first outlet.

In some embodiments, a method can comprise: flowing a cell medium through a microchannel containing at least one adhesion molecule, the cell medium comprising a first cell having a first adhesion property and a second cell having a second adhesion property; compressing the first and second cells as they flow through the microchannel, wherein the compressing causes at least one of the first and second cells to temporarily bind to the adhesion molecule; and collecting one or both of the first and second cells at a first outlet of the microchannel and collecting one or both of the first and second cells at a second outlet of the microchannel.

In some embodiments, a method can comprise: providing a cell medium to a microchannel, the cell medium comprising a first cell having a first adhesion property and a second cell having a second adhesion property, wherein the cell medium is provided to the microchannel at a flow velocity of from 10 mm/s to 300 mm/s; flowing the cell medium within the microchannel, the microchannel defining a compression gap and coated in at least one adhesion molecule, wherein the flowing comprises: compressing the first cell and the second cell as they pass through the compression gap; exposing the first cell and the second cell to the adhesion molecule, wherein the exposing causes the first and second cells to temporarily bind to the adhesion molecule; and collecting one or both of the first and second cells at a first outlet of the microchannel and collecting one or both of the first and second cells at a second outlet of the microchannel.

In some embodiments, a device capable of achieving any of the above-described methods can comprise: an inlet for flowing a cell medium comprising a plurality of cells into the device at a flow rate; a first planar wall and a second planar wall, the first planar wall having a compressive surface protruding normal to the first planar wall and defining a compression gap between the second planar wall and the compressive surface; a plurality of outlets for collecting sorted portions of the plurality of cells wherein the sorted portions share adhesion properties; and at least one adhesion molecule coating the microchannel.

In some embodiments, a system capable of achieving any of the above-described methods can comprise: a microchannel having a first planar wall and a second planar wall, the microchannel comprising a compressive surface protruding normal to the first planar wall and defining a compression gap between the second planar wall and the compressive surface, wherein the microchannel is coated with at least one adhesion molecule; a sheath inlet for flowing a cell medium into the microchannel at a flow velocity, the cell medium comprising a first cell having a first adhesion property and a second cell having a second adhesion property; a first outlet for collecting one or both of the first and second cells and a second outlet for collecting one or both of the first and second cells; wherein the plurality of cells are compressed as they flow through the compression gap, such that they temporarily bind with the adhesion molecule.

Any of the above-mentioned systems or methods can be used for sorting based on adhesion properties. Sorting based on adhesion properties of cells can be achieved by flowing cells through a microchannel. In some embodiments, the microchannel can be part of a microfluidic device.

Figure 1B:
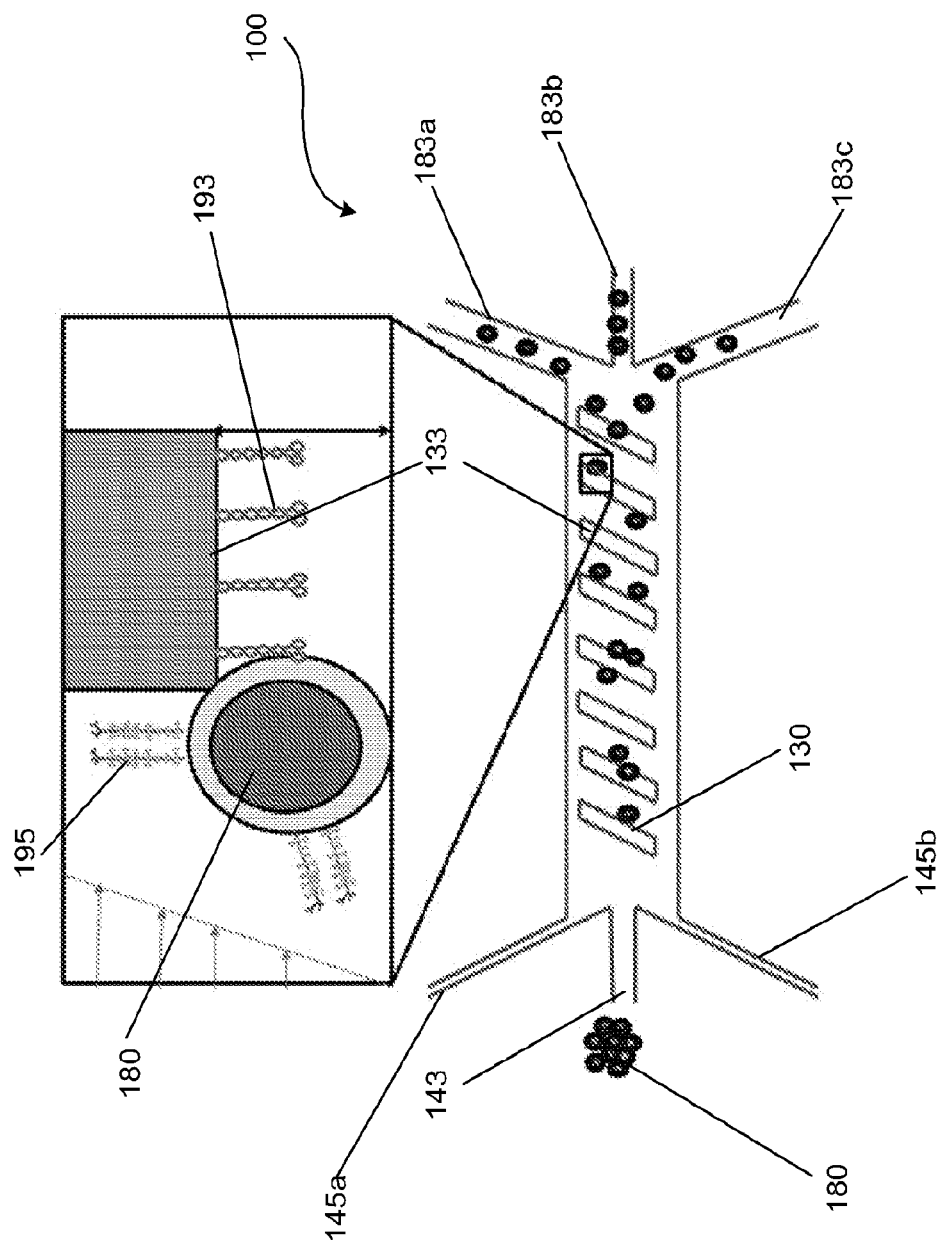
FIG. 1b is a schematic showing a three-outlet microchannel for cell sorting having a plurality of diagonal ridges, in accordance with one or more embodiments of the present disclosure.

FIGS. 1a and 1b illustrate an exemplary microchannel 100 for use in any of the above-described systems and methods. As shown in FIG. 1a, the microchannel 100 can comprise a top planar wall 110 and a bottom planar wall 120. The top planar wall 110 can comprise a plurality of compressive surfaces 130 protruding outwardly from the top planar wall 110. The microchannel 100 can comprise one or more inlets 140 provided for flowing a plurality of cells 180 and a plurality of particles 190 into the microchannel 100.

While the first and second walls of the microchannel are described with respect to FIGS. 1a and 1b as being planar, they need not be. For instance, they can be substantially planar. In other words, they can be slightly angled towards or away from each other such that they converge or diverge across a length of the microchannel. In some embodiments, they can converge or diverge more than slightly.

In some embodiments, and as illustrated at FIG. 1b, the one or more inlets 140 may include a sheath flow inlet 145a, 145b for delivering a sheath flow fluid into the microchannel 100 and a cell focusing inlet 143. The microchannel 100 can comprise a plurality of outlets 150 for collecting portions of the plurality of cells 180.

The microchannel can comprise a plurality of compressive surfaces 130. In some embodiments, the plurality of compressive surfaces 130 can comprise a plurality of ridges 133, as illustrated at FIG. 1b. The plurality of ridges 133 may be any geometric shape that is substantially elongated across the micro-channel. In some embodiments, the plurality of ridges 133 may be diagonally-oriented with respect to a central flow axis, as illustrated in FIG. 1b. The central flow axis can be located proximate a central portion of the microchannel 100 and can comprise an axis running parallel to a primary flow through the microchannel 100. As illustrated at FIG. 1b, in some embodiments, the plurality of ridges 133 can extend parallel to each subsequent ridge of the plurality of ridges. The plurality of compressive surfaces 130 may be straight, but need not be. For instance, the plurality of compressive surfaces 130 can be any shape, including but not limited to rectangular, cylindrical, trapezoidal, or triangular. Additionally, as will be understood by those skilled in the art, the plurality of compressive surfaces can comprise at least one ridge, but need not all be ridges.

The plurality of compressive surfaces 130 may define a compression gap 170 between a compressive surface 130 and a surface of an opposing wall 120, as illustrated at FIG. 1a. For instance, in an embodiment wherein the plurality of compressive surfaces 130 protrudes from the first planar wall 110, the plurality of compressive surfaces 130 may define a compression gap 170 between a compressive surface 130 and a surface across from the compressive surface 130 on the second planar wall 120. As used herein, a surface may include the closest or nearest portion of the opposing wall, for example where the wall does not otherwise have corresponding ridges or protrusions. In some embodiments, the second planar wall 120 can comprise a plurality of compressive surfaces 130, and the opposing surface can be, for example, an opposing compressive surface 130. The compression gap 170 can therefore be defined as the space formed between a compressive surface 130 and a surface of the second wall 120, or the space between opposing compressive surfaces on opposing walls. In some embodiments, the opposing ridges will be aligned with each other as well.

The size of the compression gap 170 can be increased or decreased as desired, based on device design. In some embodiments, the size of the compression gap 170 can be defined in terms of the average diameter of a cell. As will be understood, the diameter of the cell can be defined as the largest distance between two points on a cell. In some embodiments, the height of the compression gap may be defined based on a percentage of the average cell diameter. In some embodiments, the compression gap can have a height that is from 75% to 95% of the average cell size of the cells flowed through the cell sorting device (e.g., 75% to 90%, 80% to 90%, 85% to 95%, 75% to 85%, 75% to 80%, 80% to 85%, or 80% to 95%)). In some embodiments, the compression gap can have a height that is 75% or greater of the average cell size of the cells flowed through the cell sorting device (e.g., 80% or greater, 82% or greater, 84% or greater, 86% or greater, 88% or greater, 90% or greater, or 92% or greater). The compression gap can have a height that is 95% or less of the average cell size of the cells flowed through the cell sorting device (e.g., 94% or less, 92% or less, 90% or less, 88% or less, 86% or less, 84% or less, 82% or less, 80% or less, 78% or less, 76% or less). The average cell size can refer to average of the largest cross-sectional dimension of the cells flowed through the sorting device, and can be calculated using. In some embodiments, the average cell diameter can be measured using a variety of tools now known or later discovered including but not limited to optical microscopy, confocal microscopy, coulter counter, and flow cytometry.

As shown in FIGS. 1a and 1b, the plurality of compressive surfaces 130 may be separated by a flow space 160. The flow space 160 can comprise the width of a space or channel formed between a first compressive surface of the plurality of compressive surfaces and a second compressive surface of the plurality of compressive surfaces. In some embodiments, the flow space 160 may be from 50 to 1000 microns, from 50 to 750 microns, from 50 to 500 microns, from 50 to 400 microns, from 50 to 350 microns, from 100 to 300 microns, from 100 to 750 microns, from 100 to 500 microns, from 100 to 400 microns, from 100 to 300 microns, from 100 to 250 microns, or from 125 to 250 microns. The flow space 160 can be at least 50 microns, at least 100 microns, at least 125 microns, at least 150 microns, at least 250 microns, or at least 300 microns. The flow space 160 can be up to 5 microns, up to 3 microns, up to 2 microns, up to 1 microns, up to 750 microns, or up to 500 microns, 50 to 350 microns, from 100 to 300 microns, from 100 to 250 microns, from 125 to 250 microns, or at least 300 microns.

The plurality of compressive surfaces 130 may comprise an angle (a), as illustrated at FIG. 1b. The plurality of compressive surfaces 130 can be inclined at an angle to create hydrodynamic circulations underneath the compressive surfaces 130 and can be designed to compress and translate cells normal to the flow direction. The angle of the compressive surfaces 130 can also affect the trajectories of cells. The angle may vary depending on one or more parameters including, but not limited to, the types of cells flowed through the microchannel, the relaxation space 160, and the flow velocity of the medium flowed through the microchannel 100. As such, adjusting the angle may facilitate migration of cells along the compressive surfaces 130. For instance, adjusting the angle may facilitate movement of dead or damaged cells to the sides of the microchannel 100 to prevent clogging of the microchannel 100.

The angle may be increased or decreased, based on device design. For instance, in some embodiments, the angle can be from 20 to 75 degrees, from 30 to 60 degrees, from 30 to 45 degrees, at least 20 degrees, at least 30 degrees, at least 45 degrees, at least 60 degrees, or at least 75 degrees. The angle of each respective compressive surface may also be the same or different along a length of the microfluidic device. In instances where a compressive surface 130 is not linear, the angle can be measured based on a line that is a linear fit to the non-linear ridge.

The number of compressive surfaces 130 in the microchannel 110 can be increased or decreased as desired. In some embodiments, the microchannel 110 can comprise 5 to 100 compressive surfaces 130. In some embodiments, the microchannel 110 can comprise at least 3 compressive surfaces 130, at least 4 compressive surfaces 130, at least 5 compressive surfaces 130, at least 6 compressive surfaces 130, at least 7 compressive surfaces 130, at least 8 compressive surfaces 130, at least 9 compressive surfaces 130, or at least 10 compressive surfaces 130. In some embodiments, the microchannel 110 can comprise up to 100 compressive surfaces 130, up to 75 compressive surfaces 130, up to 50 compressive surfaces 130, or up to 40 compressive surfaces 130. In some embodiments, the microchannel 110 can include 5 to 50 compressive surfaces 130, 7 to 40 compressive surfaces 130, or 7 to 21 compressive surfaces 130. In some embodiments, the microchannel 110 can comprise 14 compressive surfaces 130.

The plurality of compressive surfaces 130 can be described by a thickness. The thickness can be defined as the linear measurement of the compressive surface in the direction of primary flow. The thickness can be increased or decreased as desired. In some embodiments, the thickness can be from 2 to 30 microns, from 2 to 20 microns, from 2 to 18 microns, from 2 to 16 microns, from 2 to 11 microns, from 2 to 9 microns, from 5 to 30 microns, from 5 to 20 microns, from 5 to 18 microns, from 5 to 16 microns, from 5 to 11 microns, from 5 to 9 microns from 7 to 30 microns, from 7 to 20 microns, from 7 to 18 microns, from 7 to 16 microns, from 7 to 11 microns, from 7 to 9 microns, from 9 to 20 microns, from 9 to 11 microns, from 9 to 15 microns, from 9 to 17 microns, from 9 to 30 microns, from 9 to 25 microns, from 10 to 20 microns, from 15 to 20 microns, from 15 to 30 microns, from 20 to 30 microns, from 22 to 28 microns, from 24 to 28 microns, from 18 to 21 microns, from 16 to 22 microns, or from 8 to 11 microns. In some embodiments, the thickness can be at least 2, at least 5, at least 7, at least 8, at least 9 microns, at least 11 microns, at least 15 microns, at least 16 microns, at least 18 microns, at least 20 microns, at least 22 microns, at least 24 microns, at least 25 microns, at least 27 microns and at least 30 microns.

The microchannel 100 can have one or more inlets 140. The one or more inlets 140 may be located on a first side wall of microchannel 100. In some embodiments, the microchannel 100 can have a cell focusing inlet 143 and a sheath flow inlet 145a, 145b. In some embodiments, the cell focusing inlet 143 can accomplish inertial focusing. For instance, in some embodiments, the cell inlet can be located between a first sheath flow inlet 145a and a second sheath flow inlet 145b, or can be surrounded by a first sheath flow inlet 145aa. In some embodiments, the cell focusing inlet 143 can be downstream from one or more sheath flow inlets 145a, 145b, or can be aligned with one or more sheath flow inlets 145a, 145b. A sheath fluid can allow for hydrodynamic focusing of the cell medium. The one or more sheath flow inlets 145a, 145b can be located proximate the cell flow inlet 147, or upstream of the cell flow inlet 147. Focusing the cells in the inlet can comprise providing a sheath fluid to the sheath flow inlets 145a, 145b until the sheath fluid reaches laminar flow and then subsequently introducing the cell medium cell medium through the cell inlet 147. The cells can be introduced into the cell inlet 147 by injection, for example by syringe pumps.

The described microchannel 100 can be constructed in a variety of ways. In some embodiments, the microchannel can be made using a replica molding of polydimethylsiloxane (PDMS) on a permanent mold. The mold can be created by two-step photolithography patterning of a photoresist on a 4-inch-diameter silicon wafer. After the removal of PDMS from the mold, inlet and outlet holes can be punched in the side walls of the PDMS, and the PDMS can be subsequently bonded to a glass substrate to form the microfluidic channel. As will be understood by those skilled in the art, the microchannel can be constructed of a variety of materials that may permit construction of compressive surfaces in. Additionally, in some embodiments, the systems and methods can include more than one microchannel to allow for increased and simultaneous performance of the above-described methods.

The plurality of cells 180 can be flowed into the microchannel 100 at a flow velocity. The flow velocity of any of the systems and methods described previously can be increased or decreased as desired. As used herein, the flow velocity can describe the velocity of the cell medium at an inlet or at an outlet. The flow velocity can be from 3 to 1000 mm/s, from 3 to 500 mm/s, from 3 to 250 mm/s, from 3 to 100 mm/s, from 3 to 50 mm/s, from 3 to 25 mm/s, from 3 mm/s to 10 mm/s, from 10 mm/s to 750 mm/s, from 10 mm/s to 500 mm/s, from 10 mm/s to 100 mm/s, from 10 mm/s to 50 mm/s, from 10 mm/s to 25 mm/s. The flow velocity can be at least 3 mm/s, at least 10 mm/s, at least 20 mm/s, at least t 50 mm/s, at least 100 mm/s, at least 500 mm/s, or at least 750 mm/s. The flow velocity can be 3 mm/s, 20 mm/s, 500 mm/s, 750 mm/s, or 1000 mm/s. The flow velocity can also be adjusted as a function of the length of the channel, and/or the size of the relaxation space, based on design preferences. For instance, increasing the length of the channel can allow for a greater flow velocity. Increasing the velocity in similarly sized devices can result in increased pressure within the device. By increasing the length of the microchannel, the increased pressure can be accounted for while permitting higher flow velocity. For instance, increasing the relaxation space can permit increasing the flow velocity as the greater space allows the cells a longer distance over which to travel and be subjected to secondary flow in the ridge channels. As such, increased relaxation space can permit an increased relaxation time and positive lateral displacement for certain cells despite greater flow velocity.

The microchannel can comprise a plurality of outlets 150a, 150b for collecting sorted portions of the plurality of cells. FIG. 1b illustrates an exemplary three-outlet system where a first outlet 183a may collect a first portion of cells having a first adhesion property, a second outlet 183b may collect a second portion of cells having a second adhesion property, and a third outlet 183c may collect third portion of cells having a third adhesion property By having a multiple-outlet system and modes of secondary flow (e.g. relaxation spaces between subsequent compressive spaces), the presently described systems and methods can achieve high-throughput sorting of cells based on adhesion. In some embodiments, the microchannel 100 can comprise at least two outlets, at least three outlets, at least four outlets, at least five outlets, at least seven outlets, or at least 10 outlets.

When a cell medium is flowed through the microfluidic device, cells, depending on adhesion properties, may follow unique trajectories. For instance, as illustrated at FIG. 1b, as cells flow through the microfluidic device and transiently interact with adhesion molecules coating the compressive surfaces and walls of the channel, the net forces are altered to redirect the flowing cells toward one side of the channel.

Thus, for instance, cells with high expression of the target molecule are concentrated toward one side of the channel for collection.

The cell sorting device can comprise a plurality of outlets for collecting sorted portions of the plurality of cells wherein the sorted portions share adhesion properties. For instance, in an embodiment, sorting cells based on adhesion, the cell sorting device can comprise at least two outlets wherein one outlet collects cells with high expression for a target molecule and one outlet collects cells with low expression of a target molecule. As discussed above, cells having different adhesion properties may follow unique trajectories, e.g., cells may travel through the device toward a particular outlet based on adhesion properties. As will be understood, increasing the outlets can result in more focused sorting with increased purity.

Any of the above-described outlets can include a well or chamber for pooling and/or pipetting them in the direction of a chamber or directly to a chamber. In other embodiments, the outlets can be further integrated with additional processing steps, as described below, through an integrated chip or through a capillary. Additionally, after cells are collected, any of the above-mentioned systems and methods can include an additional step of analyzing the cells using any analysis tool now known or later discovered including but not limited, flow cytometry, fluorescence microscopy, functional assays (e.g., apoptosis, cell cycle, viability, proliferation, angiogenesis), spectroscopy, immunoassays, and microplating. Additionally, in some embodiments, the microchannel and cells can be analyzed with electrode counters and microscopy.

Any of the above-described systems and methods can include a variety of cell adhesion entities. The at least one adhesion molecule can comprise one or more of selectins (e.g., E-selectins, P-selectins (PSGL1, L-selectins, etc.), integrins (e.g., an alpha integrin such as CD49a, CD49b, CD49c, CD49d, CD49e, CD49f, ITGA7, ITGA8, ITGA9, ITGA10, ITGA11, CD11D, CD103, CD11a, CD11b, CD51, ITGAW, CD11c, or a beta integrin such as CD29, CD18, CD61, CD104, ITGB5, ITGB6, ITGB7, IT), cadherins (e.g., E-cadherins, N-cadherins, P-cadherins, etc.), and immunoglobulin cell adhesion molecules (e.g., SynCAMs, NCAMs, ICAM-1, VCAM-1, PECAM-1, L1, CHL1, MAG, nectins, CD2, CD48, SIGLEC family members such as CD22 and CD83, and CTX family members such as CTX, JAMs, BT-IgSF, CAR, VSIG, and ESAM). In some embodiments, the cell adhesion entity can include proteins such as HER2. In some embodiments, the cell adhesion entity can include antibodies (including antibody fragments) that can be on the surface of the device. In some embodiments, antibodies can be co-immobilized with one or more of other cell adhesion entities. In other embodiments, the cell adhesion entity can be one or more engineered molecules now known or later discovered.

The cell adhesion entities can be disposed within or on the microchannel. In some embodiments, the cell adhesion entity can be disposed on one or more of the compressive surfaces, the first planar wall, and the second planar wall. In some embodiments, the entire microchannel can be coated in the cell adhesion entity. In other embodiments only the compressive surfaces can be coated in the cell adhesion entity. In other embodiments only one or both of the planar walls can be coated in the cell adhesion entity.

Any of the above-described systems and methods can include a variety of cells and cell types. Additionally, the cell medium may contain one or more different cell types and one or more different adhesion molecules. Any of the above-described systems and methods can achieve convective intracellular delivery of molecules into a variety of cell types. These cell types may include, but are not limited to cells of the reproductive system, e.g. oocytes, spermatozoa, leydig cells, embryonic stem cells, amniocytes, blastocysts, morulas, and zygotes; leukocytes, e.g. peripheral blood leukocytes, spleen leukocytes, lymph node leukocytes, hybridoma cells, T cells (cytotoxic/suppressor, helper, memory, naive, and primed), B cells (memory and naive), monocytes, macrophages, granulocytes (basophils, eosinophils, and neutrophils), natural killer cells, natural suppressor cells, thymocytes, and dendritic cells; cells of the hematopoietic system, e.g. hematopoietic stem cells (CD34+), proerythroblasts, normoblasts, promyelocytes, reticulocytes, erythrocytes, pre-erythrocytes, myeloblasts, erythroblasts, megakaryocytes, B cell progenitors, T cell progenitors, thymocytes, macrophages, mast cells, and thrombocytes; stromal cells, e.g. adipocytes, fibroblasts, adventitial reticular cells, endothelial cells, undifferentiated mesenchymal cells, epithelial cells including squamous, cuboid, columnar, squamous keratinized, and squamous non-keratinized cells, and pericytes and also including limbal stem cells; cells of the skeleton and musculature, e.g. myocytes (heart, striated, and smooth), osteoblasts, osteoclasts, osteocytes, synoviocytes, chondroblasts, chondrocytes, endochondral fibroblasts, and perichonondrial fibroblasts; cells of the neural system, e.g. astrocytes (protoplasmic and fibrous), microglia, oligodendrocytes, and neurons; cells of the digestive tract, e.g. parietal, zymogenic, argentaffin cells of the duodenum, polypeptide-producing endocrine cells (APUD), islets of langerhans (alpha, beta, and delta), hepatocytes, and kupfer cells; cells of the skin, e.g. keratinocytes, langerhans, and melanocytes; cells of the pituitary and hypothalamus, e.g. somatotropic, mammotropic, gonadotropic, thyrotropic, corticotropin, and melanotropic cells; cells of the adrenals and other endocrine glands, e.g. thyroid cells (C cells and epithelial cells); adrenal cells; and tumor cells.

The cells may be Burkitt lymphoma cells, choriocarcinoma cells, adenocarcinoma cells, non Hodgkin's B and T cell lymphoma cells, fibrosarcoma cells, neuroblastoma cells, plasmacytoma cells, rhabdomyosarcoma cells, carcinoma cells of the pharynx, renal adenocarcinoma, hepatoma cells, fibrosarcoma cells, myeloma cells, osteosarcoma cells, teratoma cells, teratomal keratinocytes, lung carcinoma cells, colon adenocarcinoma cells, lung adenoma cells, renal carcinoma cells, rectum adenocarcinoma cells, chronic myelogenous leukemia cells, ileocecal adenocarcinoma cells, hairy cell leukemia cells, acute myelogenous leukemia cells, colon carcinoma cells, cecum carcinoma and adenocarcinoma cells, leukemia-cecum adenocarcinoma cells, pancreatic carcinoma, Wilm's tumor cells, prostate adenocarcinoma cells, renal leimyooblastoma cells, bladder carcinoma cells, plasmacytoma cells, teratocarcinoma cells, breast carcinoma, epidermoid carcinoma of the cervix, ovarian teratocarcinoma, myeloma cells, T and B cell lymphoma cells, amalanotic melanoma cells, cervical carcinoma cells, rhabdomyosarcoma, hepatoma, medullary Thyroid carcinoma cells, malignant melanoma cells, glioblastoma cells, plasma cell leukemia, endometrial adenocarcinoma, squamous cell carcinoma, pancreatic adenocarcinoma, astrocytoma, gastric adenocarcinoma, pulmonary mucoepidermoid carcinoma cells, myeloid leukemia cells, EBV-transformed B cells, renal cell adenocarcinoma, acute leukemia, B cell plasmacytoma, acute lymphocytic leukemia, cutaneous T lymphoma, T cell leukemia, acute lymphoblastic leukemia, HIV+ T cells, medulloblastoma, B cells from sickle cell disease, acute monocytic leukemia, adrenocortical carcinoma, Bowes Melanoma and hepatocellular carcinoma.

The plurality of cells in any of the above-described systems and methods may include any of the above cells or derivatives thereof. In some embodiments, the plurality of cells can include a mixture of cell types. For instance, the cells can be part of a biological sample that can comprise a cell, a tissue, a fluid (e.g., a biological fluid), a protein (e.g., antibody, enzyme, soluble protein, insoluble protein), a polynucleotide (e.g., RNA, DNA), a membrane preparation, and the like, that can optionally be further isolated and/or purified from its native or natural state. In some embodiments, the plurality of cells can be in a "biological fluid" which can include any a fluid originating from a biological organism. Exemplary biological fluids include, but are not limited to, blood, serum, and plasma. A biological fluid may be in its natural state or in a modified state by the addition of components such as reagents, or removal of one or more natural constituents (e.g., blood plasma). A sample can be from any tissue or fluid from an organism. In some embodiments, the sample can be a biopsy. In some embodiments, the sample can comprise tissue from the breast, digestive tract, lung, liver, kidney, brain, lip, mouth, esophagus, urinary bladder, prostate, vagina, and/or cervix. In some embodiments, the sample is from a tissue that is part of, or associated with, the breast of the organism. In some embodiments, the sample may be tissue from a neoplasm. A neoplasm may include cancer. In some embodiments, the sample may be cancerous tissue or from a tumor. In some embodiments, the sample may comprise tissue surrounding cancerous tissue or a tumor. In some embodiments, the sample may comprise tissue surrounding or around the perimeter of cancerous tissue or a tumor that was surgically excised. In some embodiments, the plurality of cells being sorted comprises a mixed population of cell types. In some embodiments, the plurality of cells being sorted comprises a mixed population of cancer cells and non-cancer cells. In some embodiments, the plurality of cells being sorted comprises a mixed population of metastatic cancer cells and non-metastatic cancer cells. A cell may be a normal or healthy cell. A cell may be a neoplasatic cell. A cell may be a cancer cell. Cancer may include a carcinoma, an adenoma, a melanoma, a sarcoma, a lymphoma, a myeloid leukemia, a lymphatic leukemia, a blastoma, a glioma, an astrocytoma, a mesothelioma, or a germ cell tumor.

Additionally, any of the above-described systems and methods can include cells or cell flow medium that include fluorescent tags, dyes, antibodies, While the presently described systems and methods are described in terms of biological cells, it is understood that these presently disclosed systems and methods can be achieved using a variety of materials other than biological cells, in some embodiments, the above-described systems and methods can be achieved with a variety of particles, including nanoparticles, hydrogels, capsules, bacteria, viruses.

Additionally, any of the above-described systems and methods can include any of the above-described cells suspended in a fluid, such as a cell medium. The cell medium can be any liquid in which a plurality of cells can be suspended and can include additional substances including one or more of a carbon source (e.g., glucose) water, various salts, a source of amino acids and nitrogen (e.g., beef, yeast extract). Additionally, the medium may include other nutrients such as plant count agar, nutrient agar, trypticase soy agar, or a combination thereof.

Any of the above-described systems and methods can allow for high-throughput sorting. For instance, any of the above-described systems and methods can further comprise sorting from 10,000 to 500,000 cells/min, from 10,000 to 450,000 cells/min, from 10,000 to 400,000 cells/min, from 10,000 to 350,000 cells/min, from 10,000 to 300,000 cells/min, from 10,000 to 250,000 cells/min, from 10,000 to 200,000 cells/min, from 10,000 to 150,000 cells/min, from 10,000 to 100,000 cells/min, from 10,000 to 90,000 cells/min, from 10,000 to 80,000 cells/min, from 10,000 to 75,000 cells/min, from 10,000 to 70,000 cells/min, from 10,000 to 60,000 cells/min, from 10,000 to 50,000 cells/min, from 10,000 to 40,000 cells/min, from 10,000 to 30,000 cells/min, from 10,000 to 20,000 cells/min, from 10,000 to 15,000 cells/min, from 40,000 to 100,000 cells/min. In some embodiments, any of the above-described systems and methods can further comprise sorting at least 10,000 cells/min, at least 15,000 cells/min, at least 20,000 cells/min, at least 25,000 cells/min, at least 30,000 cells/min, at least 35,000 cells/min, at least 40,000 cells/min, at least 45,000 cells/min, at least 50,000 cells/min, at least 75,000 cells/min, at least 100,000 cells/min, at least 125,000 cells/min, at least 150,000 cells/min, at least 200,000 cells/min, at least 250,000 cells/min, at least 300,000 cells/min.

Figure 2:
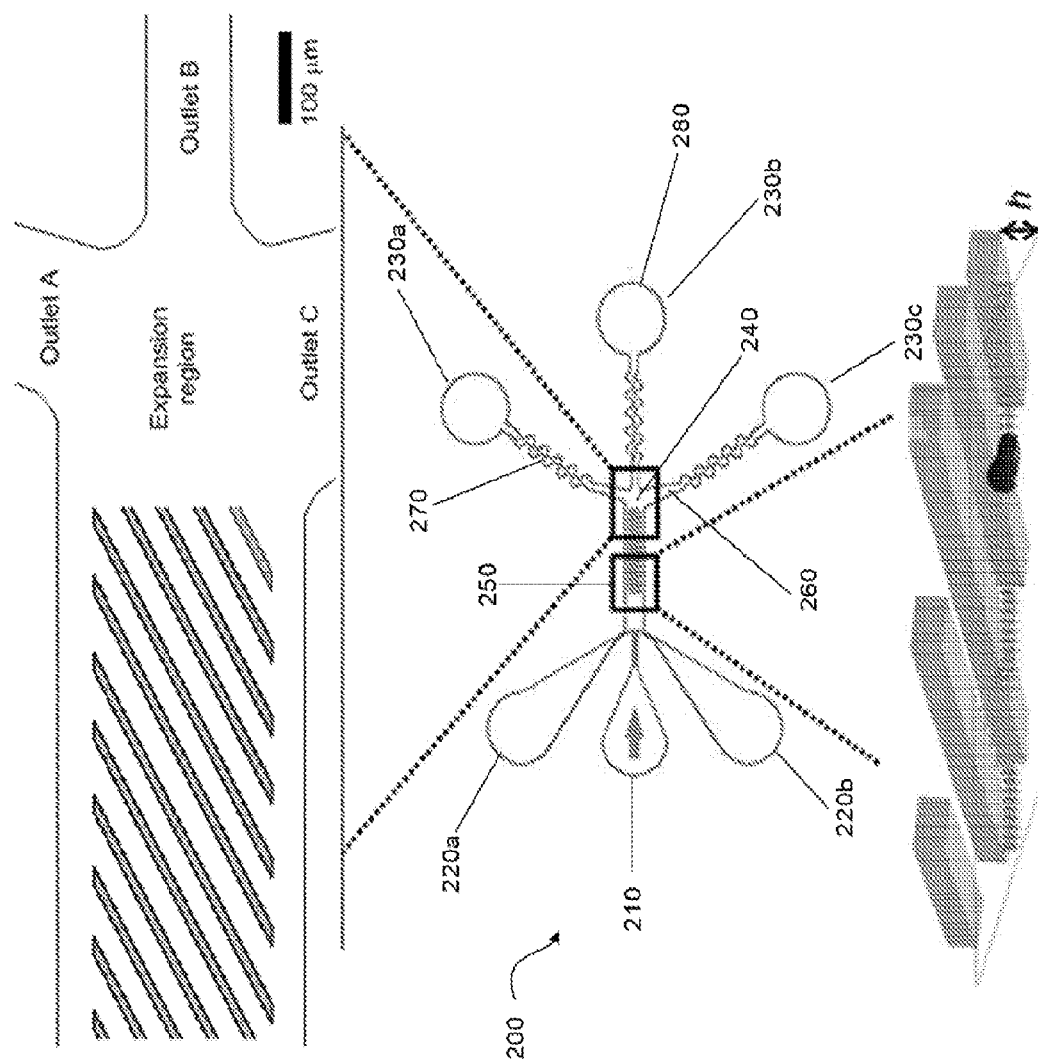
FIG. 2 is a schematic showing a three-outlet microfluidic cell sorting device having a plurality of diagonal ridges, in accordance with one or more embodiments of the present disclosure.

FIG. 2 illustrates a non-limiting example of a microfluidic device 200 can comprising three outlets (230a, 230b, 230c). The microfluidic device 200 can comprise, for example, a top outlet 230a, a central outlet 230b, and a bottom outlet 230c. As a result, the cells collected at the top 230a and bottom 230b outlets can have different expressions for a target adhesion molecule.

The disclosed microfluidic devices may comprise an expansion region and a plurality of hydrodynamically balanced outlets. FIG. 2 illustrates an exemplary and non-limiting three-outlet microfluidic device 200 comprising an expansion region 240 and three hydrodynamically balanced outlets (230a, 230b, 230c). The hydrodynamically balanced outlets (230a, 230b, 230c) can each independently comprise a flow apportionment region 260, a flow balancing region 270, and a collection point 280. The expansion region 240 can comprise a compressive surface-free portion of the microfluidic channel 250 comprising the plurality of compressive surface. The expansion region 240 can be in fluid communication with the flow apportionment regions 260 of the outlets (230a, 230b, 230c). The expansion region 240 and flow apportionment regions 260 can have an added benefit of evenly dividing channel flow amongst the outlets (230a, 230b, 230c). In some embodiments, at least one of the outlets can comprise a flow apportionment region that is larger or smaller than at least a flow apportionment region of another outlet. In a non-limiting example, as illustrated at FIG. 2, the flow apportionment region of the bottom outlet 230c is larger than the flow apportionment region of the top outlet 230a and the bottom outlet 230b.

The outlets (230a, 230b, 230c) may also each independently comprise a flow balancing region 270 and a collection point 280. The flow balancing region 270 can be downstream from and in fluid communication with the flow apportionment region 260. The collection point 280 can be downstream from and in fluid communication with the flow balancing region 270. The flow balancing region 270 can be designed so as to increase the flow resistance in the outlet and prevent flow biasing from uneven flow apportionment regions and external perturbations. The optimal architecture of the expansion region 240, flow apportionment regions 260, and flow balancing regions 270 can be determined using computational fluid dynamics to design a balanced channel flow egress across all outlets, as illustrated at FIG. 2. In a non-limiting example, and as illustrated at FIG. 2, the flow balancing regions 270 can comprise a substantially serpentine architecture. As will be understood, the flow balancing region can comprise a variety of shapes, architectures, and lengths depending on the device design.

EXAMPLES

The present disclosure is also described and demonstrated by way of the following examples. However, the use of these and other examples anywhere in the specification is illustrative only and in no way limits the scope and meaning of the disclosure or of any exemplified term. Likewise, the disclosure is not limited to any particular embodiments described here. Indeed, many modifications and variations of the disclosure may be apparent to those skilled in the art upon reading this specification, and such variations can be made without departing from the disclosure in spirit or in scope.

Example 1—Continuous Sorting of Cells Based on Differential P Selectin Glycoprotein Ligand Expression Using Molecular Adhesion In an exemplary embodiment, the above-described systems and methods can include a microfluidic platform capable of high throughput separation of cells by differences in molecular adhesion. The device can operate by flowing cells through a ridged microchannel such that the surfaces are decorated with cell adhesion entity (e.g. an adhesion molecule) providing specificity to a cell surface receptor. As cells transiently interact with ligands at the ridge and wall interfaces, the net forces can be altered to redirect the flowing cells toward one side of the channel. Thus, cells with high expression of the target molecule can be concentrated toward one side of the channel for collection. One unique aspect of this sorting design is the ridge gap spacing (e.g. a compression gap) that optimizes cell compressions to increase the surface area for interaction between the ligand on cell surface and coated receptor molecule, but without sufficient strain to unduly influence the cell trajectory by biomechanical properties such as stiffness and viscoelasticity. Thus, ridge compression can be used to optimize adhesive interactions in a manner that cell stiffness does not influence the cell separation mechanism. As a result, receptor-specific cell separation can occur while maintaining a high flow rate and throughput. By designing chips with multiple outlets, the sorting is capable of fractionation of cells based upon the amount of receptor expressed.

To demonstrate cell separation, lectin molecules were used, which previously have been used for sorting cells though affinity columns. Since cell binding to lectins depends on factors like metabolic state, stage of cell division, and differentiation, the method is useful for applications like isolating stem cells based on differentiation or homing potential. Of these lectin-based sorting, P selectin and P selectin glycoprotein ligand 1 (PSGL-1) sorting was chosen due to the potential applications in understanding the role of PSGL in T cell immune response and developing effective therapeutics. Therefore, in this study, PSGL-1/P selectin, ligand-receptor binding is used to sort target cells.

Experimental Methods

Microfluidic Device Fabrication.

Microfluidic sorting devices were designed in SolidWorks. The microfluidic devices with different gap size were fabricated by replica molding Polydimethylsiloxane (PDMS) on a permanent mold. The mold was made from SU-8 2007 using a two mask photolithography process. The mold dimensions were characterized with profilometry (Dektak 150 proflier) and verified with confocal microscopy imaging (Olympus LEXT).

Uncured PDMS was mixed in a 10:1 ratio of elastomer to curing agent (Sygard 184 elastomer kit), then poured onto the SU-8 molds to a thickness of 1 cm and cured in an oven at 60° C. for 6 h. The cured PDMS layer was peeled off the mold, cut into chips, and inlet and outlet holes were formed with a 1 mm biopsy punch. The PDMS device was treated with oxygen plasma (Harrick plasma cleaner) for 2 min then bonded to a glass microscope slide. The ridged microchannels were designed to have gap sizes of 9.3 µm for Jurkat cells and 10.3 µm for HL60 cells, which imposes a cellular strain of 15% on each cell type. The channel width was 560 µm and length was 3.8 mm with 25 skew ridges equally spaced along the channel length. The ridges were 20 µm wide and distance between two consecutive ridges was 70 µm. The ridges were at the top of the microchannel and are inclined at a 30 degree. Three and five outlet devices were used to study the resolution of separation.

Sample Preparation and Experimental Setup.

Jurkat cells (CRL-1990) and HL60 (CCL 240) were used. Cells were cultured and maintained in RPMI-1640 medium with the addition of 10% FBS and 1% penicillin-streptomycin. Cells were incubated at 37° C. supplied with 5% carbon dioxide. Recombinant human P selectin was resuspended in PBS at a concentration of 3 µg/mL. The assembled device was degassed in a vacuum chamber for 10 min, filled with P-selectin solution (3 microliters/mL) by pipetting, and then incubated at room temperature. After 3 h incubation, the device was washed with 1% bovine serum albumin (BSA). Cells suspended in medium at $0.5 \times 10^6$ or $1 \times 10^6$ cells/mL were flowed into the device at 0.045 and 0.1 mL/min using syringe pump. A high-speed camera (Phantom V7.3 149 Vision Research) and inverted microscope setup is used as described previously. Following collection at outlets, cells are incubated at 37° C. with blocking solution for 15 min and then incubated for 30 min with primary monoclonal antibodies and then, after a wash with PBS, incubated with fluorescently labeled secondary antibodies for 30 min at final concentrations of 30 and 50 µg/mL respectively. Between primary and secondary antibodies incubation and after secondary antibody incubation and flow analysis, cells were washed with PBS. To detect cell-surface PSGL-1, mouse antihuman PSGL-1 clone KPL-1 was used, followed by secondary antibody PE-conjugated goat antimouse IgG. Solutions composed of primary and secondary antibodies were preincubated for at least 1 h prior to incubation with cells. Cells were analyzed with flow cytometer. Fluorescent imaging was used to check the degree of detachment of P selectin from cells after flow experiment. For this purpose, 1% FITC BSA was used as a blocking agent. To measure the activation of cells, antibodies, anti CD69-FITC, and CD11b-APC were used according to manufacturer's manual. Three sets of experiments were conducted for the study of cell activation. In the first experiment, incubated Jurkat cells were incubated with P selectin for 24 h at 37° C. with 5% carbon dioxide. In the second experiment, Jurkat cells were incubated for 2 h with P selectin coated PDMS surface, in which the PDMS surface was first activated by incubating it with P selectin for 3 h at room temperature, at 37° C. with 5% carbon dioxide. In the third experiment, Jurkat cells were collected after sorting through the proposed device. Expressions of CD69 and CD11b were compared for all the three experiments using flow cytometry.

Cell Stiffness Measurement with Atomic Force Microscopy.

Atomic force microscopy was used to measure the stiffness of cells. All cells were measured in suspended states after slight attachment to the surface. To measure cells in suspended state, a monolayer of poly-L-lysine was grafted onto the glass slide substrate. This operation provided anchorage of the cell to the glass substrate while maintaining roundedness of morphology for cells and improved the cell stability during the AFM measurements. The AFM experiment was carried out immediately after the washing step and poly-L-lysine cell attachment treatment and all measurements were finished within 2 hours. A change in measured stiffness was not observed during the course of these measurements. Measurements were conducted using a MFP-3D AFM attached to an inverted optical microscope. A silicon nitride cantilever with a spring constant measured to be 37.1 pN/nm and a spherical tip was positioned above the center of individual cells before indentation. The Young's modulus is a function of loading force and loading rate. The force-indentation curve was obtained for each measurement at a 40% strain and then analyzed with a Hertzian model for a spherical tip from which the Young's modulus values were calculated.

Fluid Flow Simulations.

Finite element simulations of fluid flow were performed using COMSOL Multiphysics software. Simulations were performed for channel width of 560 µm and ridge inclination angles of 30°. PDMS was selected as the material of interfacing structure. The flow profiles in the channel were obtained by solving the Navier-Stokes equations for incompressible fluid using fluid-structure interaction physics. At the outlet, the pressure was set to zero with no viscous stress on the boundary. Because of low Reynolds number of the fluid, it was assumed that the suspended particles would follow the fluid streamlines.

Results and Discussion

Figure 3A:
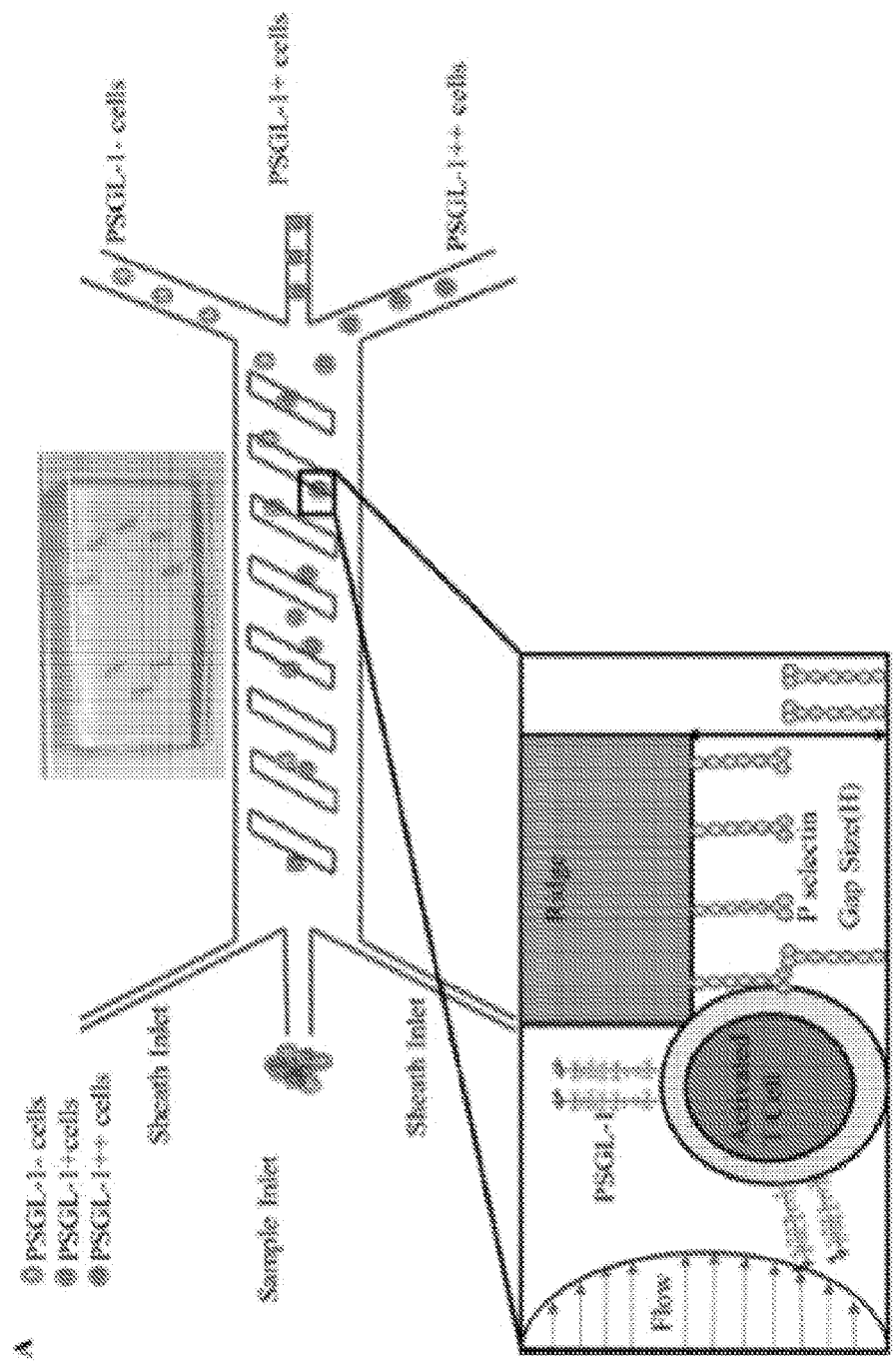
FIG. 3a is an adhesion-based sorting device, in accordance with one or more embodiments of the present disclosure.
Figure 3B:
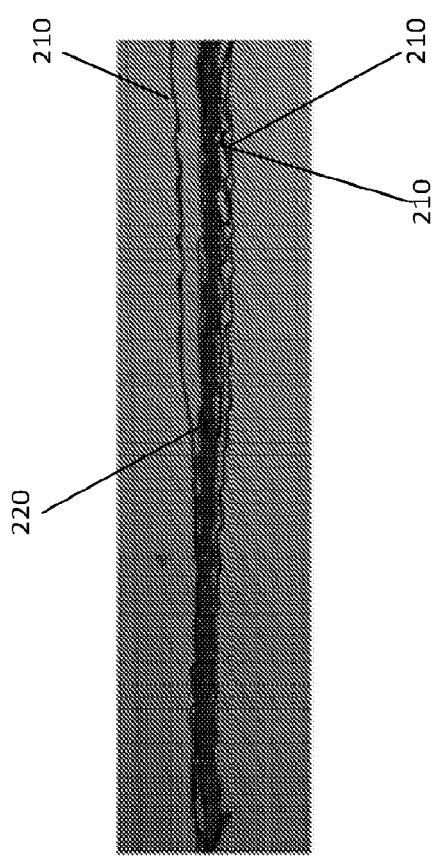
FIG. 3b shows the trajectories of Jurkat cells flowing through an adhesion-based sorting device, in accordance with one or more embodiments of the present disclosure.

The sorting device shown in FIG. 3a uses the flow of cells through a microchannel decorated with diagonal ridges and selectin coated bottom glass surface on cells as they flow results in a net lateral displacement that distributes the cells at different y positions hence at different outlets based on the binding between P selectin on device surface and PSGL-1 on cell surface. The cells flowing in the device without P selectin follow the fluid streamlines as no adhesion is observed in this case. The unique aspect of this sorting design is the use of optimized gap size height, which can include the distance between the ridge and bottom of the channel, to lightly squeeze the cells while flowing under the ridged part of the channel while offering a high surface area for specific interaction between the cells and ligand molecules coated on the ridges. FIG. 3b shows the trajectory of Jurkat cells flowing through the device with (black, 210) and without (blue, 220) P selectin coating. Jurkat cells without P selectin coating tended to follow trajectories to towards the side edges of the channel whereas Jurkat cells with P selectin coating tended to follow a trajectory through the middle of the channel.

To understand the sorting of cells by expression of PSGL-1, the behavior of two model leukocytes flowing in the device was examined, HL60 and Jurkat cell lines. The gap size in each case was optimized so that biomechanical compression forces resulting from stiffness and viscoelasticity were minimized so as not to dominate the cell separation process. In these flow experiments, 9.3 µm gap size was used for adhesive sorting of Jurkat cells, which is larger than prior gap sizes reported for stiffness separation of cells of 8 µm. Thus, the 9.3 µm gap size is sufficient to lightly squeeze Jurkat cells, which have a diameter of 11 µm, but large enough that stiffness does not dominate the sorting. In the case of HL60 cells, a 10.3 µm gap size was used as these cells are 12 µm in diameter. Specificity to PSGL-1 expression was obtained through device functionalization by ligands found on surface of HL60 and Jurkat cells and shows binding to P selectin coated surfaces.

Figure 4:
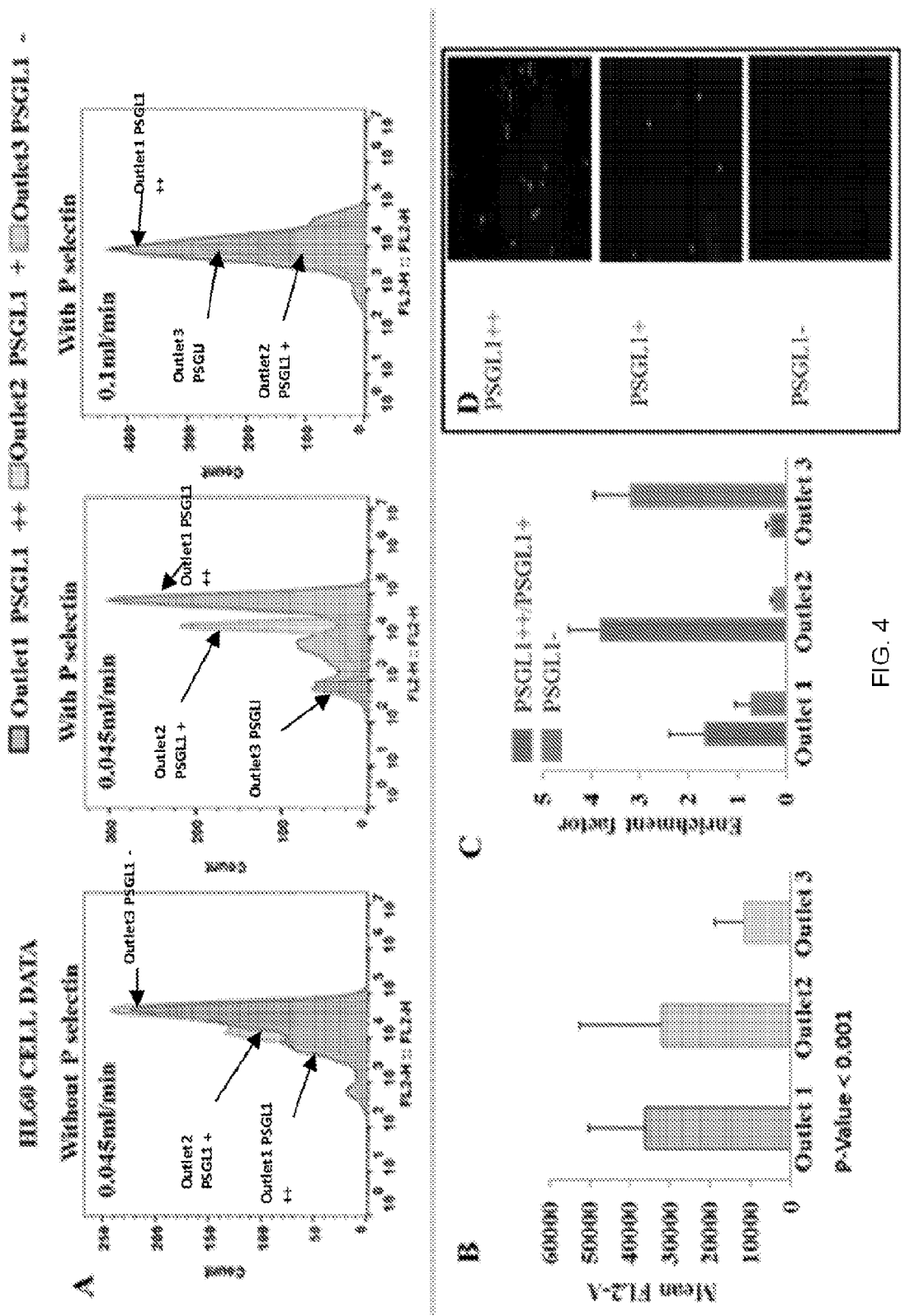
FIG. 4 shows various graphical representations illustrating enrichment and fractionation of HL60 cells through adhesion, in accordance with one or more embodiments of the present disclosure.

To characterize the sorting of different cell types by the device, the sorted cells were examined after incubating them with primary and secondary antibodies using protocol described in methods with flow cytometry. For both HL60 and Jurkat cells, cells were separated based on expression of PSGL-1 ligand by using a single, ridged channel coated with P selectin. HL60 cells were flowed at flow rates of 0.045 and 0.1 mL/min in the device with P selectin incubation and at 0.045 mL/min without P selectin incubation. The flow cytometry data for outlets for the three different cases are shown in FIG. 4 at (A). Adhesion dependence of outputs faced an upper limit of flow rate in which sorting of PSGL-1 positive cells at high flow rates was diminished, as shown in FIG. 4 at (A), which shows flow cytometer data for HL60 cells collected at different outlets, including the peak shift in their mean fluorescent values. FIG. 4 at (B) shows the fluorescent mean values of collected sample at different outlets for 0.045 mL/min flow rate with P selectin incubation. A two-way ANOVA and Tukey tests were performed on the collected data to show a significant difference in fluorescent mean values of three outlets. The utilized flow rate of 0.045 mL/min was substantially higher than that used in other microfluidic label-free adhesion based sorting. 3.8 and 3.2-fold enrichment of PSGL-1 positive and negative HL60 cells respectively was demonstrated, as shown in FIG. 4 at (C). Fluorescent microscopy was also used to validate outlet characterization of the device, as shown in FIG. 4 at (D)D. The PSGL-1++ outlet in FIG. 4 at (D)D shows more cells with secondary antibody attached to them, hence showing more PSGL-1 expression.

Figure 5:
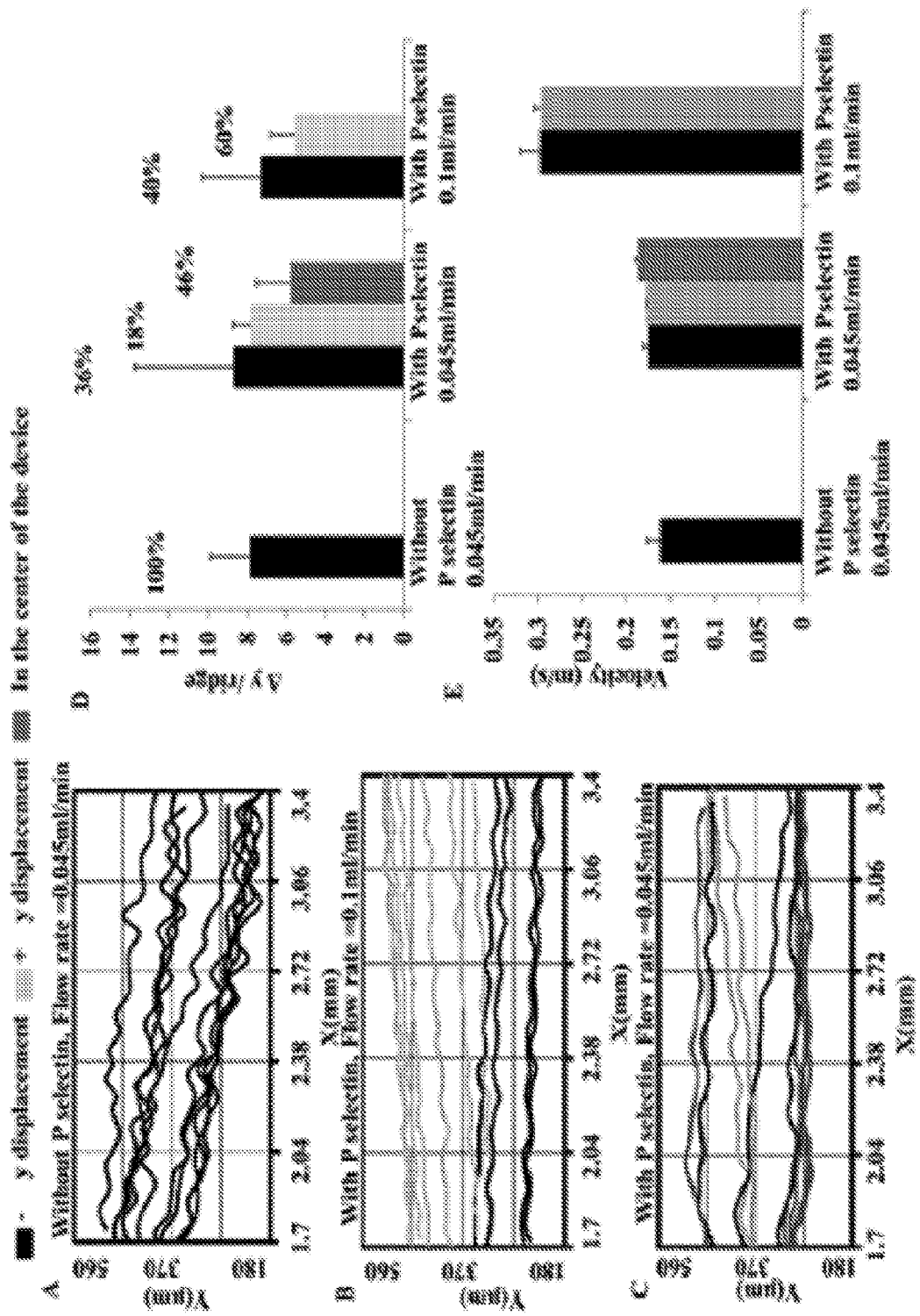
FIG. 5 shows various graphical representations illustrating trajectories of HL60 cells with and without P selectin incubated device at different flow rates, in accordance with one or more embodiments of the present disclosure.

FIG. 5 at (A) analyzes the trajectory of HL60 cells with and without P selectin functionalization and at increased flow rates. In FIG. 5 at (B), the data from trajectories was extracted to determine the lateral displacement of cell flows between two ridges, defined as Δy/ridge. The trajectories for uncoated devices showed displacement only in the negative y direction; whereas, the P-selectin coated device showed displacement with a range of values, either positive, negative, or in the middle of the device.

Analysis of trajectories of cells at high flow rate of 0.1 mL/min for P selectin coated device in FIG. 5 at (D) and (E) shows that 40% of the cells are displaced in negative y direction with 7.3 µm and 60% in positive y direction with 5.3 m Δy/ridge and at much higher velocities as compared to 0.045 mL/min flow rate. This lack of enrichment at high flow rates (FIG. 4 at (A), right) indicates hydrodynamic forces dominate adhesive forces, in part due to larger hydrodynamic forces and in part to insufficient time for cells to form adhesions with the coated surface. Therefore, low enrichment of cells based on adhesion was observed at a flow rate of 0.1 mL/min.

Figure 6:
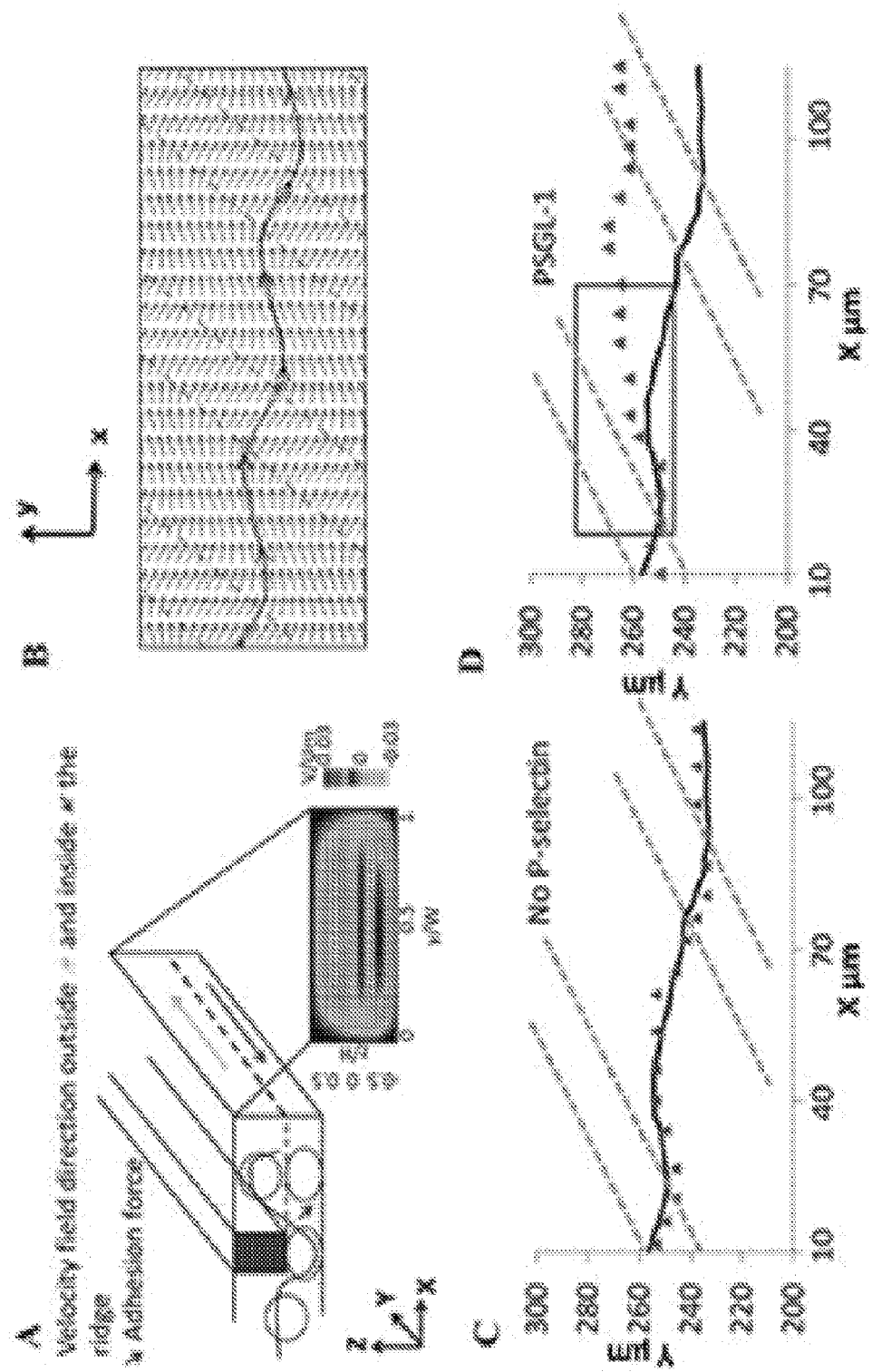
FIG. 6 shows various graphical representations illustrating trajectories of cells based on PSGL-1 expression, in accordance with one or more embodiments of the present disclosure.

The working mechanism of the device is explained in FIG. 6 at (A). As cells flow under the ridge, they bind to P-selectin and when leaving the ridges cells with more ligand expressed on their surface resist the secondary drag force and stay adhered to the bottom of the channel and flow in a negative y direction (red arrow). On the other hand, cells with less ligand expression detach and pull away from the surface and enter the streamline in a positive y direction (green arrow). Cells flowing through the device without P selectin coated ridges move with the fluid flow streamlines. The trajectories of Jurkat cells are compared with COMSOL streamline at height equals to half of the gap size in xy-plane in FIG. 6 at (B)-(D). Cells closely follow the simulated streamline in the case of a device with no P selectin. Since cells in the stream are located near the bottom channel wall with weak elastic force and no adhesion force, they are transported by the circulating flow created by the ridges in the negative transverse direction, as shown in FIG. 6 at (B). In the case of less PSGL-1 on the cell surface (FIG. 6 at (C)), as a cell leaves the ridge, it is pulled off and detached from the surface and follows the streamlines that moves up in y direction. On the other hand, a cell with more PSGL-1 (FIG. 6 at (D)) attaches to the surface once it enters the ridge and rolls nearly straight on the bottom glass surface as it leaves the ridge.

Figure 7:
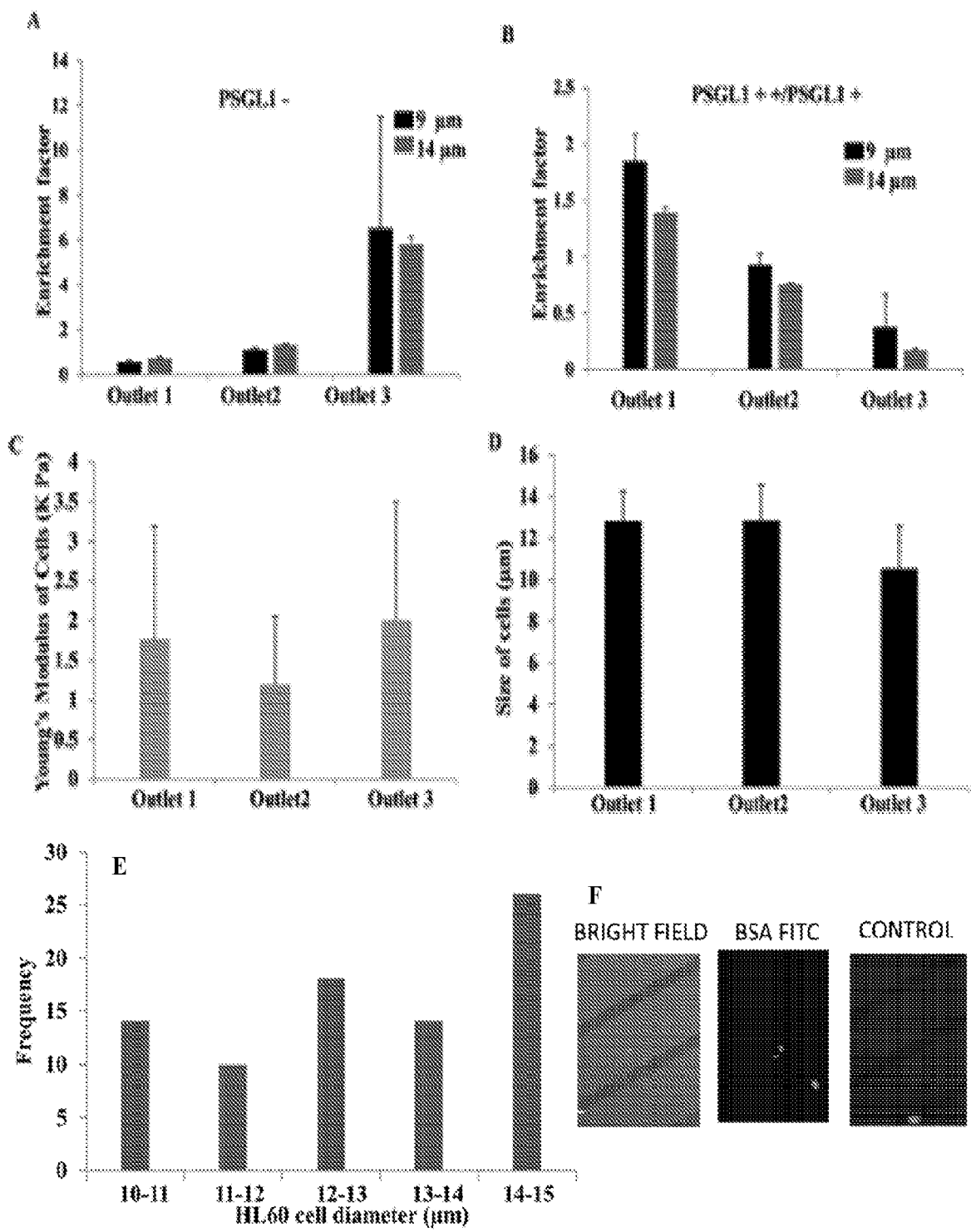
FIG. 7 shows various graphical representations illustrating the effects of gap size on cell enrichment, in accordance with one or more embodiments of the present disclosure.

In previous studies, gap sizes ranging from 4 to 12 μm were tested for sorting Jurkat cells by stiffness and found that an 8 μm gap size gave optimal sorting based on biophysical differences with minimal occlusion. On the basis of these conclusions, gap sizes of 9 and 14 μm were tested to evaluate sensitivity to adhesion differences without sensitivity to stiffness differences. As can be seen in FIG. 7 at (A) and (B), increasing the gap size decreases the enrichment factor because of a decrease in cell strain, which leads to decrease in surface area for interaction between cell surface and coated device. After cell separation, the stiffness of the cells collected at the three outlets was also examined, as shown in FIG. 7 at (C). A lack of significant difference in stiffness indicates that stiffness was not a determining factor in cell sorting. The measured cell size distribution, representing the average plus and minus the standard deviation of HL60 cells, was between 10.0 and 15.4 μm (FIG. 7 at (E)). From this distribution and the ridge gap dimension, approximately 8% of cells were exposed to <3% cell strain and 92.7% of cells were exposed to cell strain from 3% to 33%. A threshold of >40% cell strain is required for cell stiffness to dominate the sorting mechanism in a ridged microchannel. While large cell heterogeneity in size or stiffness may indeed impact adhesion separation, for the conditions of this study, cell stiffness did not vary at the sorting outlets. It was anticipated that if cell heterogeneity significantly exceeded that studied here, i.e. if cell size variation exceeded 25%, then decreased accuracy of adhesion dependence is expected. Fluorescent imaging of the device (FIG. 7 at (F)) after the flow experiment verified that P selectin was not significantly removed after flow experiments and remained intact throughout the flow experiment. The device after the flow experiment (middle image of FIG. 7 at (F)) showed no fluorescence and hence P selectin is intact after flow experiment.

Figure 8:
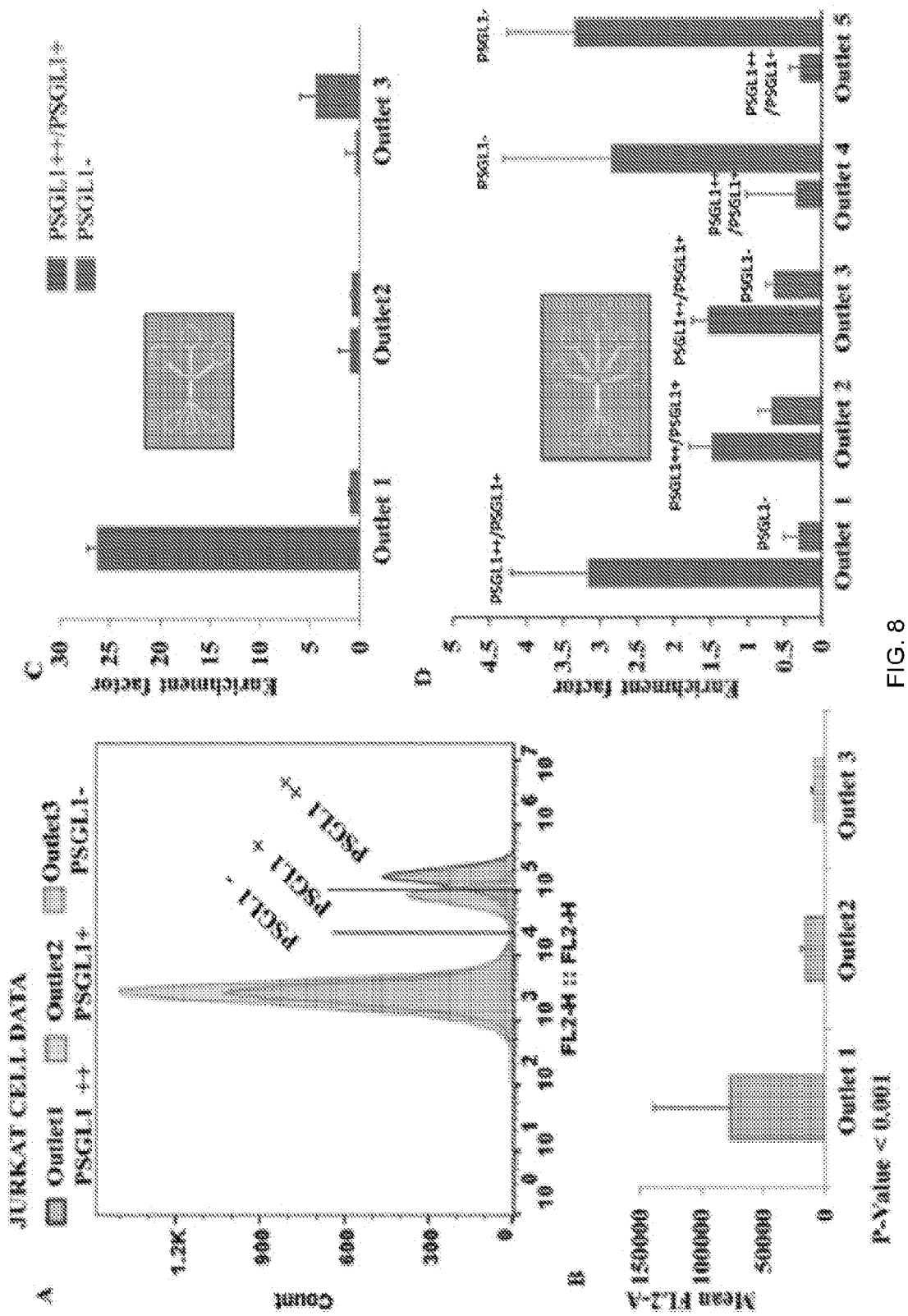
FIG. 8 shows adhesion-based fractionation of cells, in accordance with one or more embodiments of the present disclosure.

FIG. 8 at (A) shows the flow cytometer data for Jurkat cells collected at different outlets showing a peak shift in their mean fluorescent values. FIG. 8 at (B) shows mean fluorescent intensity at each outlet. 26-fold and 4.4-fold enrichment of PSGL-1 positive and negative Jurkat cells respectively was demonstrated, as shown in FIG. 8 at (C). Fractionation of a single cell type based on the expression of a ligand at high flow rates and with significant population enrichment was demonstrated, as shown in FIG. 8 at (D)d. One potential application for fractionation of T cells is sorting based on the density of specific chimeric antigen receptors (CAR). Potential targets for CAR-based therapies are cell surface antigens expressed at higher densities on cancer cells. Generally, this may lead to severe adverse effects due to the recognition of minimal Ag expression outside the target tumor. The microfluidic sorting device can therefore be used to determine threshold Ag densities for CAR-based therapies in order to avoid off target tumor toxicity.

Figure 9:
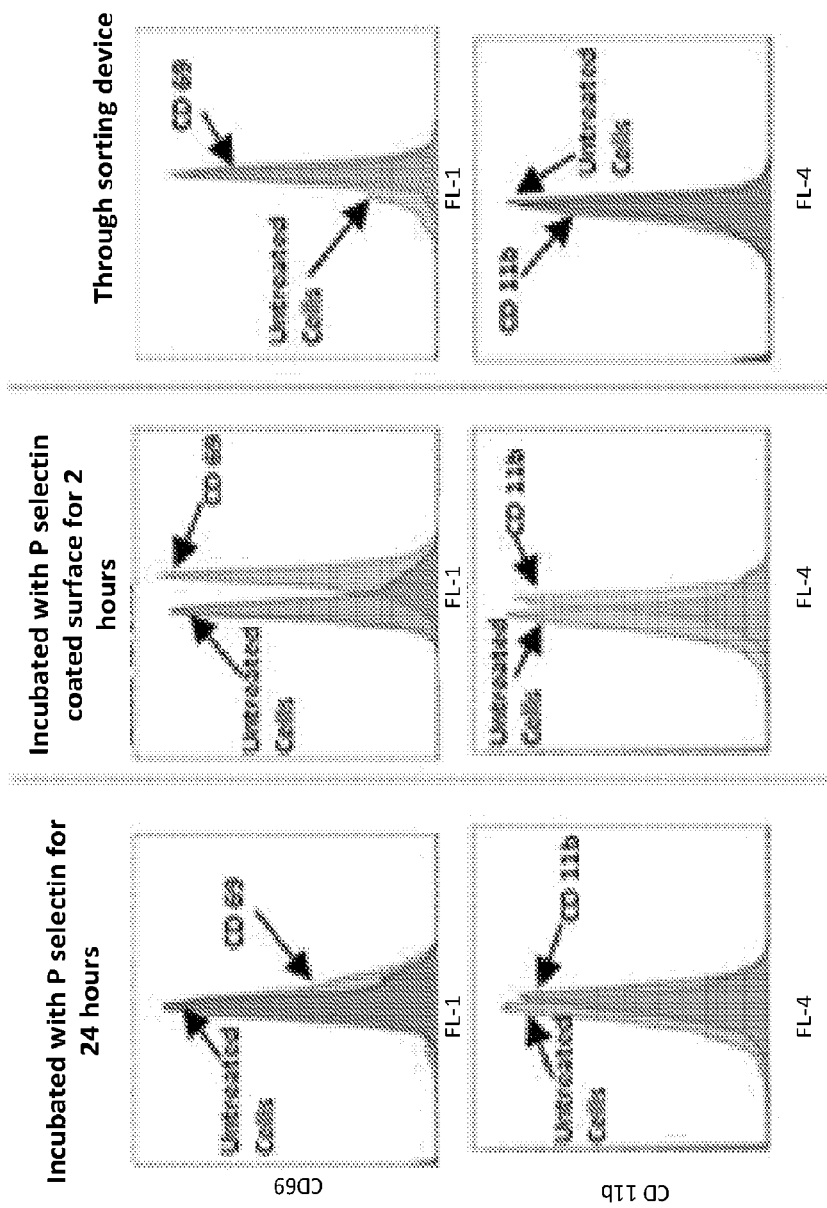
FIG. 9 shows results of a study analyzing activation of sorted cells using CD69 and CD11b staining, in accordance with one or more embodiments of the present disclosure.

A concern of adhesion-based isolation methods is the modification and activation of the target cells after isolation by long-term binding (greater than 1 hour). Beads used for binding and pull-down isolation can activate cells. Studies have also indicated that engagement of selectin ligands on leucocytes directly transduces signals. For example, interactions of PSGL-1 with immobilized P-selectin rapidly induce tyrosine phosphorylation of multiple proteins. However, the present data show that increase in tyrosine phosphorylation is observed at least 2 min after P selectin and PSGL-1 binding. The above-described systems and methods provide another application where cell sorting is possible without cell activation due to very short binding contact between receptor and ligand. Three sets of experiments were conducted in order to compare activation of cells due to short-term binding of PSGL-1 and P selectin in the microfluidics sorting approach. To test activation of the sorted cells (data presented is for Jurkat cells), CD69 staining and CD11b were used to detect the activation of cells as classical markers. The results in FIG. 9 show a slight up regulation of activation markers after cells are incubated with P selectin for 24 hour but very significant change when removed from P selectin coated surface. In FIG. 9, results are compared with cells incubated with P selectin for 24 hours and with cells incubated with P selectin coated surface for 2 hours. There is a significant up regulation of activation markers after cells removed from P selectin coated surface. There was no change in expression of activation markers in case of cells collected after sorting. Also, no change in shape was observed. Taken together, these results indicate sorting produces no cell activation due to very short binding time (<10 ρs) between P selectin and PSGL-1 while cells are flowing through the shear in the device and the association and dissociation were sufficiently gentle so as not activate cells. In this work, HL60 cell line were separated at a final concentration of 106 cells/mL at a flow rate of 45 μL/min which resulted in a throughput of approximately 45,000 cells per minute. The high throughput is over 2 orders of magnitude higher than previous microfluidic approaches using asymmetric adhesive patches that require cell rolling to maintain contact. The improvement results from the ability to flow cells at a faster velocity due to the forced contact at the narrow-gap ridges.

CONCLUSION

A microfluidic device capable of high throughput separation of cells by differences in specific cell adhesion has been demonstrated. Adhesion is mediated by specific adhesive events from cell surface PSGL-1 receptors to surface immobilized selectins. The device displays sufficient sensitivity to adhesion so that differential receptor expression can be distinguished and enriched. 26-fold and 3.8-fold enrichment of PSGL-1 positive and 4.4-fold and 3.2-fold enrichment of PSGL-1 negative Jurkat and HL60 cells have been demonstrated, respectively. Enrichment of PSGL-1 positive Jurkat cells to 3-fold using a five-outlet fractionation device has also been demonstrated. This is the first study that shows fractionation of single cell line based on the ligand it expresses at high flow rates with significant population enrichment. Heterogeneity in cell stiffness or size show minimum effect on sorting at optimized gap size. Because of the skewed ridge design, no clogging was observed and ability to clear cells with less interrupted fluid flow. Further, applications using the device to sort desired cell phenotypes with high throughput are possible to allow downstream purification and analysis.

The ligand-based sorting also has potential applications in understanding the role of PSGL-1 in T cell immune response and developing effective therapeutics. It has been reported that PSGL-1 on T cells dampens TCR signals, limits survival of effector T cells, and promotes immune inhibitory receptor expression, thereby supporting establishment of exhaustion in viral and tumor models. PSGL-1-deficiency enhances T cell antitumor immunity to melanoma, promotes viral control and T cell survival is reported to be increased in PSGL-1 deficit T cells after chronic virus infection. The above-described systems and methods also offer direct measurement of transient nature interaction between important physiological ligands and interacting cells. It can be used as a tool to monitor stem cell differentiation. It also has potential applications in measuring degree of changes in adhesion signature of cancer cells, hence better therapeutics. Unlike MACS and panning, the separation can fractionate by the amount of surface antigen on a cell and also eliminate the limitation posed by the choice of antibodies is limited within a pool of commercially available antibodies, which in turn limits the separation targets to those cells with specific markers.

While several possible embodiments are disclosed above, embodiments of the present disclosure are not so limited. These exemplary embodiments are not intended to be exhaustive or to unnecessarily limit the scope of the disclosure, but instead were chosen and described to explain the principles of the present i disclosure so that others skilled in the art may practice the disclosure. Indeed, various modifications of the disclosure in addition to those described herein will become apparent to those skilled in the art from the foregoing description. Such modifications are intended to fall within the scope of the appended claims. Such changes are intended to be embraced within the scope of the disclosure. The embodiments of the present disclosure are also not limited to the particular formulations, process steps, and materials disclosed herein as such formulations, process steps, and materials may vary somewhat. Further, the terminology employed herein is used for the purpose of describing exemplary embodiments only and the terminology is not intended to be limiting since the scope of the various embodiments of the present disclosure will be limited only by the appended claims and equivalents thereof.

The specific configurations, choice of materials, and the size and shape of various elements can be varied according to particular design specifications or constraints requiring a device, system, or method constructed according to the principles of the disclosure. Such changes are intended to be embraced within the scope of the disclosure. The presently disclosed embodiments, therefore, are considered in all respects to be illustrative and not restrictive, and those skilled in the art will understand that variations and modifications can be effected within the scope of the disclosure as defined in the appended claims. The scope of the disclosure is therefore indicated by the following claims, rather than the foregoing description and above-discussed embodiments, and all changes that come within the meaning and range of equivalents thereof are intended to be embraced therein.

We claim:

1. A method comprising:
   providing cells to a microchannel, the microchannel coated in a cell adhesion entity and comprising compressive surfaces and a first outlet, the compressive surfaces:
      formed by ridges oriented at an angle of from 25 degrees to 70 degrees measured with respect to a center axis of the microchannel; and
      defining compression gaps, each having a height of from 75% to 95% of an average diameter of the cells;
   compressing the cells through the microchannel, wherein the compressing comprises flowing the cells through the compression gaps which exposes the cells to the cell adhesion entity, wherein the exposing causes:
      a first portion of the cells having a first adhesion property relative to the cell adhesion entity to follow a first trajectory through the microchannel and temporarily bind to the cell adhesion entity; and
      a second portion of the cells having a second adhesion property relative to the cell adhesion entity to follow a second trajectory through the microchannel;
      wherein the first adhesion property is different from the second adhesion property; and
      wherein the first trajectory is different from the second trajectory; and
   collecting the first portion of the cells at the first outlet.

2. The method of claim 1, wherein the microchannel further comprises a first wall and a second wall, the first wall and the second wall being substantially planar to each other; and
   wherein the compressive surfaces protrude in a direction normal to the first wall and define the compression gaps between the compressive surface and the second wall.

3. The method of claim 1, wherein a flow space is disposed between an adjacent pair of the compressive surfaces along the center axis of the microchannel.

4. The method of claim 3, wherein a width of the flow space, along the center axis, is from 50 to 500 microns.

5. The method of claim 1, wherein providing the cells through the microchannel further comprises providing a sheath flow of a cell medium, to cause the cell medium to flow through the microchannel.

6. The method of claim 1, wherein first adhesion property is defined by a cell surface receptor; and
   wherein the cell adhesion entity temporarily binds to the cell surface receptor.

7. The method of claim 1, wherein the first trajectory is determined based on the first adhesion property; and
   wherein the second trajectory is determined based on the second adhesion property.

8. The method of claim 1 further comprising collecting the second portion of the cells at a second outlet spaced away from the first outlet.

9. The method of claim 1, wherein the compressing further comprises creating hydrodynamic circulations of the cells within the compression gaps.

10. The method of claim 1, wherein the angle at which the ridges are oriented varies along the center axis of the microchannel.

11. The method of claim 1, wherein the ridges have a thickness that varies along the center axis of the microchannel.

12. The method of claim 1, wherein the cell adhesion entity is positioned on the compressive surfaces.

13. The method of claim 1, wherein the cell adhesion entity is positioned only on the compressive surfaces.

14. The method of claim 2, wherein the cell adhesion entity is positioned on the compressive surfaces, the first wall, and the second wall.

15. The method of claim 1, wherein the microchannel is coated in more than one type of cell adhesion entity; and
   wherein different types of the cell adhesion entity are positioned on different ones of the compressive surfaces.

16. The method of claim 1, wherein providing the cells to the microchannel comprises providing a biological fluid comprising the cells to the microchannel.

17. The method of claim 16, wherein the biological fluid is selected from the group consisting of blood, serum, and plasma.

18. The method of claim 1, wherein providing the cells to the microchannel comprises providing a cell medium comprising the cells to the microchannel.

19. The method of claim 18, wherein the cell medium is selected from the group consisting of a carbon source, water, a salt, an amino-acid source, and a nitrogen-source.

20. The method of claim 1 further comprising controlling flow resistance through the first outlet with a flow balancing region.

\* \* \* \* \*